United States Patent
Zuend et al.

(10) Patent No.: US 11,014,863 B2
(45) Date of Patent: May 25, 2021

(54) HYDROFORMYLATION METHOD FOR THE LARGE-SCALE PRODUCTION OF ALDEHYDES AND/OR ALCOHOLS

(71) Applicant: BASF SE, Ludwigshafen am Rhein (DE)

(72) Inventors: Stephan Zuend, Fremont, CA (US); Rainer Papp, Ludwigshafen am Rhein (DE); Boris Breitscheidel, Ludwigshafen am Rhein (DE); Armin Lange De Oliveira, Heidelberg (DE)

(73) Assignee: BASF SE, Ludwigshafen am Rhein (DE)

( * ) Notice: Subject to any disclaimer, the term of this patent is extended or adjusted under 35 U.S.C. 154(b) by 13 days.

(21) Appl. No.: 16/613,307

(22) PCT Filed: May 14, 2018

(86) PCT No.: PCT/EP2018/062328
§ 371 (c)(1),
(2) Date: Nov. 13, 2019

(87) PCT Pub. No.: WO2018/210720
PCT Pub. Date: Nov. 22, 2018

(65) Prior Publication Data
US 2021/0078925 A1    Mar. 18, 2021

(30) Foreign Application Priority Data

May 16, 2017  (EP) ..................... 17171250

(51) Int. Cl.
| C07C 29/00 | (2006.01) |
| B01J 23/00 | (2006.01) |
| C07C 29/149 | (2006.01) |
| B01J 23/72 | (2006.01) |
| C07C 31/12 | (2006.01) |

(52) U.S. Cl.
CPC ............. *C07C 29/149* (2013.01); *B01J 23/72* (2013.01); *C07C 31/12* (2013.01)

(58) Field of Classification Search
CPC .................................................. C07C 29/149
See application file for complete search history.

(56) References Cited

U.S. PATENT DOCUMENTS

| 3,501,537 A | 3/1970 | Johnson, Jr. et al. |
| 4,148,830 A | 4/1979 | Pruett et al. |
| 4,190,731 A | 2/1980 | Nehring et al. |
| 5,004,845 A | 4/1991 | Bradley et al. |
| 5,395,990 A * | 3/1995 | Scarlett ............ C07C 29/149 568/864 |
| 6,051,163 A | 4/2000 | Kumberger et al. |
| 6,100,432 A | 8/2000 | Borgel et al. |
| 6,511,583 B1 | 1/2003 | Müller et al. |
| 6,680,414 B2 | 1/2004 | Knoop et al. |
| 6,723,884 B1 | 4/2004 | Grenacher et al. |
| 6,727,391 B2 | 4/2004 | Walczuch et al. |
| 6,765,119 B2 | 7/2004 | Hoffmann et al. |
| 7,510,591 B2 | 3/2009 | Huber-Dirr et al. |
| 10,030,120 B2 | 7/2018 | Wagner et al. |

FOREIGN PATENT DOCUMENTS

| AU | 20004112100 A | 10/2000 |
| DE | 2445303 A1 | 4/1976 |
| DE | 2628987 A1 | 1/1978 |
| DE | 2740216 B1 | 2/1979 |
| DE | 3228881 A1 | 2/1984 |
| DE | 19914260 A1 | 10/2000 |
| EP | 0073129 A1 | 3/1983 |
| EP | 0901982 A1 | 3/1999 |
| EP | 0846095 B1 | 10/2000 |
| EP | 1165480 A1 | 1/2002 |
| EP | 1219584 A2 | 11/2002 |
| EP | 1255720 A2 | 11/2002 |
| EP | 1673332 A1 | 6/2006 |
| GB | 1512797 A | 6/1978 |
| GB | 1579159 A | 11/1980 |
| WO | WO-9734694 A1 | 9/1997 |
| WO | WO-0058255 A1 | 10/2000 |
| WO | WO-0114297 A1 | 3/2001 |
| WO | WO-0158844 A1 | 8/2001 |
| WO | WO-01087809 A1 | 11/2001 |
| WO | WO-2004085356 A1 | 10/2004 |
| WO | WO-2005028407 A1 | 3/2005 |
| WO | WO-2015082676 A1 | 6/2015 |

OTHER PUBLICATIONS

International Preliminary Report on Patentability for PCT/EP2018/062328 dated Apr. 18, 2019.
International Search Report for PCT/EP2018/062328 dated Aug. 10, 2018.
Written Opinion of the International Searching Authority for PCT/EP2018/062328 dated Aug. 10, 2018.

* cited by examiner

*Primary Examiner* — Sikarl A Witherspoon
(74) *Attorney, Agent, or Firm* — Faegre Drinker Biddle & Reath LLP

(57) ABSTRACT

A process for preparing $C_4$ to $C_{13}$ monohydroxy compounds from a bottom fraction arising in the distillation of a crude mixture of $C_4$ to $C_{13}$ oxo-process aldehydes from cobalt-catalyzed or rhodium-catalyzed hydroformylation, or in the distillation of a crude mixture of $C_4$ to $C_{13}$ oxo-process alcohols, which comprises contacting the bottom fraction in the presence of hydrogen with a catalyst comprising copper oxide and aluminum oxide, at a temperature of 150° C. to 300° C. and a pressure of 20 bar to 300 bar and subjecting the resulting crude hydrogenation product to distillation, and the amount of $C_4$ to $C_{13}$ monohydroxy compounds present in the crude hydrogenation product after the hydrogenation being greater than the amount of $C_4$ to $C_{13}$ monohydroxy compounds given stoichiometrically from the hydrogenation of the ester and aldehyde compounds present in the bottom fraction, including the $C_4$ to $C_{13}$ monohydroxy compounds still present in the bottom fraction before the hydrogenation.

9 Claims, No Drawings

HYDROFORMYLATION METHOD FOR THE LARGE-SCALE PRODUCTION OF ALDEHYDES AND/OR ALCOHOLS

CROSS-REFERENCE TO RELATED APPLICATIONS

This application is a national stage application (under 35 U.S.C. § 371) of PCT/EP2018/062328, filed May 14, 2018, which claims benefit of European Application No. 17171250.8, filed May 16, 2017, both of which are incorporated herein by reference in their entirety.

Hydroformylation processes serve industrial production of aldehydes and/or alcohols. Hydroformylation processes can in general be subdivided, according to the nature of the catalyst used, into cobalt-catalyzed or rhodium-catalyzed hydroformylation processes. Rhodium-catalyzed hydroformylation processes can be subdivided in turn into high-pressure and low-pressure rhodium processes. Low-pressure rhodium processes may take the form either of a gas circulation process or of a liquid discharge process.

Industrially relevant hydroformylation processes are set out for example in Falbe, New Syntheses with Carbon Monoxide, Springer Berlin, 1980, pages 162 to 176 and in Ullmann's Encyclopedia of Industrial Chemistry, 2013 Wiley-VCH, Weinheim, doi10.1002/14356007.a8_312. pub2, pages 1 to 4.

The preparation of aldehydes by hydroformylation is accomplished through the reaction of olefins in the presence of a hydroformylation catalyst, carbon monoxide, and hydrogen. The aldehydes obtained through hydroformylation have one carbon atom more than the olefins employed.

Because of the reductive conditions prevailing during the hydroformylation, it is possible for the aldehydes to be reduced at least partially to give the corresponding alcohols.

Depending on the nature of the hydroformylation process and on the hydroformylation conditions selected, it is possible to exert influence over the aldehyde selectivity, the hydrogenation activity, and the n:iso ratio (see, for example, Ullmann's Encyclopedia of Industrial Chemistry, 2013, Wiley-VCH, Weinheim, doi:10.1002/14356007.a18_321.pub2).

Aldehydes, being reactive compounds, undergo a variety of reactions even during the hydroformylation that lead to formation of byproducts, or to formation of complex byproduct mixtures. Since these byproducts usually have a higher molar mass and thus higher boiling temperatures than the hydroformylation products, these byproducts are also referred to as high-boiling byproducts.

High-boiling byproducts are formed, for example, by aldol condensation, Tischenko reaction, transesterification reactions and/or disproportionation reactions, as dimers, trimers and/or tetramers, from the hydroformylation products. High-boiling byproducts are typically obtained in the form of aldehydes, esters, acetals and/or diols.

Hence U.S. Pat. No. 4,148,830 describes by way of example the formation of various high-boiling byproducts from the hydroformylation products of the hydroformylation of propene. According to U.S. Pat. No. 4,148,830, the high-boiling byproducts are formed, for example, by aldol condensation, Tischenko reaction, transesterification reactions and/or disproportionation reactions, as dimers, trimers and/or tetramers, in the form of aldehydes, esters, acetals and/or diols.

Hydroformylation products generally comprise the aldehydes which are prepared by hydroformylation and which have one carbon atom more than the olefins employed. Owing to the reductive conditions prevailing during the hydrogenation, the hydroformylation products may also comprise alcohols, originating from the hydrogenation of the above aldehydes, or else mixtures of aldehydes and alcohols.

Removing the high-boiling byproducts from the hydroformylation products is done differently from one hydroformylation process to another. For example, the high-boiling byproducts may be removed in a step together with the hydroformylation catalyst, or in a process step subsequent to the removal of the hydroformylation catalyst. Where the high-boiling byproducts are removed in a process step subsequent to the removal of the hydroformylation catalyst, this is generally done as part of the further working-up of the hydroformylation products.

In the case of cobalt-catalyzed hydroformylation, the high-boiling byproducts are present together with the hydroformylation catalyst and the hydroformylation products in the discharge from the hydroformylation. To remove the hydroformylation catalyst, it is converted into a water-soluble form and then removed by liquid extraction. One advantageous configuration of such a process is described for example in WO 01/14297. The high-boiling byproducts can be removed from the hydroformylation products subsequently during the further working-up of these hydroformylation products.

In the gas circulation process oftentimes employed for the hydroformylation of propene, the hydroformylation products are discharged in the gas phase at the top or close to the top of the hydroformylation reactor. High-boiling byproducts and the hydroformylation catalyst in this case remain in the hydroformylation reactor. The gaseous discharge is condensed and the hydroformylation products are freed from unreacted olefin, hydrogen, carbon monoxide, and lower-boiling byproducts, such as propane. The hydroformylation products are subsequently passed on for further working up. Following removal of propane and compression, unreacted olefin, hydrogen, and carbon monoxide are recycled to the hydroformylation reactor.

In the liquid discharge process oftentimes used for the hydroformylation of propene or butenes, the hydroformylation catalyst and the high-boiling byproducts can be removed from the hydroformylation products by supplying, for example, the hydroformylation discharge comprising hydroformylation products, hydroformylation catalyst, and high-boiling byproducts to a distillation, in which the hydroformylation catalyst and the high-boiling byproducts are obtained in the bottom fraction and the hydroformylation products in the top fraction. The hydroformylation products arising in the top fraction can then be passed on for further working up. It is an advantage, however, if the hydroformylation discharge is first depressurized in one or more stages, with the discharge being separated at each depressurization stage into a liquid phase and a gaseous phase. By this means it is possible, for example, to remove byproducts boiling lower than the hydroformylation products, and unreacted olefin, hydrogen and/or carbon monoxide, from the hydroformylation discharge. The gaseous phase and the liquid phase which arise at the last depressurization stage are passed subsequently in countercurrent in a distillation column, with the hydroformylation products being obtained in the top fraction and the high-boiling byproducts with the hydroformylation catalyst in the bottom fraction. The high-boiling byproducts and the hydroformylation catalyst can be returned to the hydroformylation reaction or supplied for working-up of the hydroformylation catalyst. Advantageous embodiments of the process are disclosed for example in EP-A 0846095 or EP-A 1255720. The hydroformylation products obtained in the top fraction can subsequently be passed on for further working up.

When the hydroformylation catalyst has been largely removed from the hydroformylation products, optionally together with the high-boiling byproducts, the crude mixture of hydroformylation products obtained as a result is worked up further. The further working-up generally comprises distillative purification and/or hydrogenation.

For a crude mixture of hydroformylation products having 4 or 5 carbon atoms, the distillative purification may be accomplished, for example, by the process described in EP-A 1 165 480. For a crude mixture of hydroformylation products having 6 to 13 carbon atoms, the distillative purification may be accomplished, for example, by the process described in DE-A 199 14 260, although that process is disclosed only for alcohols.

Hydrogenation of the hydroformylation products produces a crude mixture of hydrogenation products. The hydrogenation may be supplied with a crude mixture of hydroformylation products or with largely pure hydroformylation products as obtained, for example, after the distillative purification of a crude mixture of hydroformylation products.

Hydrogenation products comprise alcohols. Since the hydrogenation products originate from the hydrogenation of the hydroformylation products, the hydrogenation products have one carbon atom more than the olefins used for the hydroformylation.

The hydrogenation of the hydroformylation products, or of a crude mixture of hydroformylation products, takes place by methods known to the skilled person. In general the hydrogenation takes place in the presence of hydrogen over a catalyst. The hydrogenation represents a process step downstream of the hydroformylation.

The catalysts used are generally heterogeneous catalysts. The catalysts preferably comprise as their catalytically active component metals and/or metal oxides from groups VI to VIII and also the $1^{st}$ transition group of the Periodic Table of the Elements, more particularly chromium, molybdenum, manganese, rhenium, iron, cobalt, nickel and/or copper. The catalytically active component is preferably deposited on a carrier material. The carrier material comprises $Al_2O_3$, $SiO_2$ and/or $TiO_2$, for example. Such catalysts are described for example in DE-A 3228881, DE-A 2628987, and DE-A 2445303. The aldehydes are hydrogenated using the stoichiometric amount of hydrogen, or an excess of hydrogen. There is a general preference for using an excess of hydrogen. Thus, for example, an excess of 1.5 to 20 percent over the amount of hydrogen needed stoichiometrically to hydrogenate the aldehydes may be used. The aldehydes are hydrogenated in general at a temperature of 50 to 200° C. and at a hydrogen pressure of 25 to 350 bar. In order to avoid secondary reactions it is preferred for a small amount of water to be added to the hydrogenation feed in accordance with DE-A 2628987. There is a further preference for the hydrogenation feed to be admixed with an aqueous solution of an alkali metal hydroxide or carbonate in accordance with the disclosure content of WO 01087809.

The resulting crude mixture of hydrogenation products is supplied for further working up. The further working-up of the crude mixture of hydrogenation products generally comprises a distillative purification.

For a crude mixture of hydrogenation products having 4 or 5 carbon atoms, the distillative purification may be accomplished, for example, in analogy to the process described for aldehydes in EP-A 1 165 480. For a crude mixture of hydrogenation products having 6 to 13 carbon atoms, the distillative purification may be accomplished, for example, in analogy to the process described in DE-A 199 14 260.

In view of the thermal load on the hydroformylation products or hydrogenation products during further working up, especially during the hydrogenation and/or the distillative purification, it is possible here as well for high-boiling byproducts to be formed. High-boiling byproducts may form, for example, in analogy to U.S. Pat. No. 4,148,830 by aldol condensation, Tischenko reaction, transesterification reactions and/or disproportionation reactions of the aldehydes, or from the reaction between aldehyde and alcohol.

In the distillative purification of the crude mixture of the hydroformylation products or of the crude mixture of the hydrogenation products, the high-boiling byproducts are obtained in the bottom fraction.

Since the high-boiling byproducts have only limited economic usefulness, they are mostly passed on for energy recovery.

A further possibility for obtaining utility from high-boiling byproducts, or from a bottom fraction including these byproducts, is disclosed for example in DE-B 2740216. Hence DE-B 2740216 describes a process for working up distillation residues from the hydroformylation of propene. These distillation residues are esterified under acid catalysis in the presence of n-butanol or isobutanol, and the resulting esters are separated by distillation from the catalyst and from unutilizable high boilers, such as diols, and then hydrogenated over a copper chromite catalyst. Products of value obtained include n- and isobutanol and 2-ethylhexanol.

U.S. Pat. No. 3,501,537 as well discloses a process for working up high-boiling byproducts obtained as distillation residues in the hydroformylation of propene. The distillation residues are in this case subjected to repeated distillation in order to remove the hydroformylation catalyst. The distillate obtained in this process is then hydrogenated directly over a copper chromite catalyst or else hydrogenated in a two-stage process, first over a nickel catalyst and subsequently over a copper chromite catalyst.

The intention in U.S. Pat. No. 5,004,845, according to its description, is to provide a process wherein the losses of alcohol through formation of byproducts during the catalytic hydrogenation of $C_2$ to $C_{10}$ aldehydes are to be minimized. For this purpose it appears to prove advantageous for esters which are formed as byproducts during the catalytic hydrogenation to be recycled to the catalytic hydrogenation, following removal from the alcohols, in order thereby to exert a favorable influence over the equilibrium of the reactions which take place during the hydrogenation.

It was an object of the present invention to provide a process for converting these high-boiling byproducts, formed during the hydroformylation or the further working-up of a crude mixture of hydroformylation products or of a crude mixture of hydrogenation products, into products of value. In the context of the present invention, products of value are short-chain alcohols of the kind obtained, for example, as hydrogenation products through hydrogenation of the hydroformylation products. By means of the process of the invention it is to be possible to convert high-boiling byproducts in the form of acetals and/or diols into products of value and thus to increase the yield of products of value.

The object is achieved by means of a process for preparing $C_4$ to $C_{13}$ monohydroxy compounds, preferably $C_4$ to $C_9$ monohydroxy compounds, from a bottom fraction arising in the distillation of a crude mixture of $C_4$ to $C_{13}$ oxo-process aldehydes, preferably $C_4$ to $C_9$ oxo-process aldehydes, from cobalt-catalyzed or rhodium-catalyzed hydroformylation, or in the distillation of a crude mixture of $C_4$ to $C_{13}$ oxo-process alcohols, preferably $C_4$ to $C_9$ oxo-process alcohols, which comprises contacting the bottom fraction in the presence of hydrogen with a catalyst comprising copper oxide (CuO) and aluminum oxide, at a temperature of 150° C. to 300° C. and a pressure of 20 bar to 300 bar and subjecting the resulting crude hydrogenation product to distillation, and the amount of $C_4$ to $C_{13}$ monohydroxy compounds, preferably $C_4$ to $C_9$ monohydroxy compounds, present in the crude hydrogenation product after the hydrogenation being greater than the amount of $C_4$ to $C_{13}$ monohydroxy compounds, preferably $C_4$ to $C_9$ monohydroxy compounds, given stoichiometrically from the hydrogenation of the ester and aldehyde compounds present in the bottom fraction, including the $C_4$ to $C_{13}$ monohydroxy compounds, preferably $C_4$ to $C_9$ monohydroxy compounds, still present in the bottom fraction before the hydrogenation.

Where the hydroformylation products comprise aldehydes, the hydroformylation products are also referred to as oxo-process aldehydes. As already mentioned, these aldehydes have one carbon atom more than the olefins used for the hydroformylation.

Oxo-process alcohols are obtained by hydrogenation of oxo-process aldehydes. Hence oxo-process alcohols may be obtained, for example, by hydroformylation using ligand-modified cobalt carbonyl complexes as hydroformylation catalysts (see, for example, Falbe, New Syntheses with Carbon Monoxide, Springer Berlin, 1980, pages 167 to 168), or by separate hydrogenation of the hydroformylation products when the latter comprise oxo-process aldehydes.

A crude mixture of oxo-process aldehydes is a mixture substantially comprising oxo-process aldehydes and from which the hydroformylation catalyst has been largely removed. A crude mixture of oxo-process aldehydes may include high-boiling byproducts.

A crude mixture of $C_4$ to $C_{13}$ oxo-process aldehydes is a mixture which comprises substantially oxo-process aldehydes with the same carbon number and from which the hydroformylation catalyst has been largely removed. A crude mixture of $C_4$ to $C_{13}$ oxo-process aldehydes may include high-boiling byproducts.

Thus a crude mixture of $C_4$ oxo-process aldehydes comprises n-butanal, isobutanal, or a mixture thereof, with the mixing ratio of n-butanal to isobutanol being dependent on the reaction conditions of the hydroformylation. A crude mixture of $C_5$ oxo-process aldehydes comprises, for example, valeraldehyde, isovaleraldehyde, 2-methylbutyraldehyde, or a mixture thereof, with the mixing ratio being dependent on the reaction conditions and on the hydroformylation feedstocks (see, for example, EP-B1 1673332). A crude mixture of $C_6$ oxo-process aldehydes comprises, for example, capronaldehyde, 2-methylpentan-1-al, 3-methylpentan-1-al, 4-methylpentan-1-al, 2,2-dimethylbutan-1-al, 2,3-dimethylbutan-1-al, 3,3-dimethylbutan-1-al, 2-ethylbutan-1-al, or a mixture of two, three, four or more of the stated $C_6$ oxo-process aldehydes. A crude mixture of $C_7$ oxo-process aldehydes comprises, for example, n-heptanal or isoheptanal. A crude mixture of $C_8$ oxo-process aldehydes comprises, for example, 2-ethyl-2-hexenal, n-octanal or isooctanal. A crude mixture of $C_9$ oxo-process aldehydes comprises, for example, n-nonanal or isononanal. A crude mixture of $C_{10}$ oxo-process aldehydes comprises, for example, 2-propylheptanol, n-decanal or isodecanal. A crude mixture of $C_{11}$ oxo-process aldehydes comprises, for example, n-undecanal or isoundecanal. A crude mixture of $C_{12}$ oxo-process aldehydes comprises, for example, n-dodecanal or isododecanal. A crude mixture of C oxo-process aldehydes comprises, for example, n-tridecanal or isotridecanal.

A crude mixture of oxo-process alcohols is a mixture which comprises substantially oxo-process alcohols and from which the hydroformylation catalyst has been largely removed. A crude mixture of oxo-process alcohols may comprise high-boiling byproducts. A crude mixture of oxo-process alcohols may be obtained, for example, by hydrogenation of pure oxo-process aldehydes, or by hydrogenation of a crude mixture of oxo-process aldehydes.

A crude mixture of $C_4$ to $C_{13}$ oxo-process alcohols comprises a mixture which substantially comprises oxo-process alcohols with the same carbon number and from which the hydroformylation catalyst has been largely removed. A crude mixture of $C_4$ to $C_{13}$ oxo-process alcohols may comprise high-boiling byproducts.

Thus a crude mixture of $C_4$ oxo-process alcohols comprises n-butanol, isobutanol, or a mixture thereof. A crude mixture of $C_5$ oxo-process alcohols comprises, for example, n-pentanol, 2-methyl-1-butanol, 3-methyl-1-butanol, or a mixture of two, three or more of the stated $C_5$ oxo-process alcohols. A crude mixture of $C_6$ oxo-process alcohols comprises, for example, n-hexanol, 2-methylpentan-1-ol, 3-methylpentan-1-ol, 4-methylpentan-1-ol, 2,3-dimethylbutan-1-ol, 2-ethylbutan-1-ol, or a mixture of two, three, or more of the stated $C_6$ oxo-process alcohols. A crude mixture of $C_7$ oxo-process alcohols comprises, for example, n-heptanol or isoheptanol. A crude mixture of $C_8$ oxo-process alcohols comprises, for example, 2-ethylhexanol, n-octanol or isooctanol. A crude mixture of $C_9$ oxo-process alcohols comprises, for example, n-nonanol or isononanol. A crude mixture of $C_{10}$ oxo-process alcohols comprises, for example, 2-propylheptanol, n-decanol or isodecanol. A crude mixture of $C_{11}$ oxo-process alcohols comprises, for example, n-undecanol or isoundecanol. A crude mixture of $C_{12}$ oxo-process alcohols comprises, for example, n-dodecanol or isododecanol. A crude mixture of $C_{13}$ oxo-process alcohols comprises, for example, n-tridecanol or isotridecanol.

The preparation of $C_4$ to $C_{13}$ oxo-process aldehydes and $C_4$ to $C_{13}$ oxo-process alcohols is known to the skilled person or is available to that person from their common general knowledge (see, for example, Ullmann's Encyclopedia of Industrial Chemistry, 2013 Wiley-VCH and Weinheim, doi:10.1002/14356007.a1_321.pub3, Ullmann's Encyclopedia of Industrial Chemistry, 2013 Wiley-VCH, Weinheim, doi:10.1002/14356007.a01_279.pub2).

$C_4$ to $C_{13}$ monohydroxy compounds obtained by the process of the invention comprise individual compounds or isomer mixtures. Depending on the carbon number, it may be possible to separate the isomer mixtures into their individual compounds by distillation.

$C_4$ monohydroxy compounds are n-butanol, isobutanol or a mixture thereof. $C_5$ monohydroxy compounds are n-pentanol, 2-methyl-1-butanol and 3-methyl-1-butanol or a mixture of two, three or more of the stated $C_5$ monohydroxy compounds. Isomer mixtures of $C_4$ or $C_5$ monohydroxy compounds may be separated into their individual compounds generally by distillation, as for example by the process disclosed in EP-A 1 165 480. Although the process in EP-A1 1 165 480 is disclosed for aldehydes, it can also be utilized for the distillation of $C_4$ or $C_5$ monohydroxy compounds. Hence isomer mixtures of $C_4$ monohydroxy compounds can be separated by distillation into n-butanol and isobutanol, for example. Monohydroxy compounds having more than 5 carbon atoms in the chain are generally obtained from the distillation as an isomer mixture. The distillation of monohydroxy compounds having 6 to 13 carbon atoms may be accomplished, for example, by the process described in DE-A1 199 14 260. Hence $C_6$ monohydroxy compounds are obtained generally as n-hexanol or as an isomer mixture. $C_7$ monohydroxy compounds are obtained generally as n-heptanol or as an isomer mixture. $C_8$ monohydroxy compounds are obtained generally as 2-ethylhexanol, n-octanol or isooctanol. $C_9$ monohydroxy compounds are obtained generally as n-nonanol or isononanol. $C_{10}$ monohydroxy compounds are obtained generally as 2-propylheptanol, n-decanol or isodecanol. $C_{11}$ monohydroxy compounds are obtained generally as n-undecanol or isodecanol. $C_{12}$ monohydroxy compounds are obtained generally as n-dodecanol or isododecanol. $C_{13}$ monohydroxy compounds are obtained generally as n-tridecanol or isotridecanol.

The process of the invention is suitable for preparing $C_4$ to $C_{13}$ monohydroxy compounds from a bottom fraction. Preferentially the process of the invention is suitable for preparing $C_4$ to $C_9$ monohydroxy compounds, more preferably for preparing $C_4$ or $C_9$ monohydroxy compounds, and very preferably for preparing $C_4$ monohydroxy compounds.

A bottom fraction which is used in the process of the invention arises in the distillation of a crude mixture of $C_4$ to $C_{13}$ oxo-process aldehydes or in the distillation of a crude mixture of $C_4$ to $C_{13}$ oxo-process alcohols. Preferably a bottom fraction which is used in the process of the invention arises in the distillation of a crude mixture of $C_4$ to $C_9$ oxo-process aldehydes or in the distillation of a crude mixture of $C_4$ to $C_9$ oxo-process alcohols. With further preference a bottom fraction which is used in the process of the invention arises in the distillation of a crude mixture of $C_4$ or $C_9$ oxo-process aldehydes or in the distillation of a crude mixture of $C_4$ or $C_9$ oxo-process alcohols. With particular preference a bottom fraction used in the process of the invention arises in the distillation of a crude mixture of $C_4$ oxo-process aldehydes or $C_4$ oxo-process alcohols.

It is possible for a bottom fraction arising in the distillation of a crude mixture of $C_4$ to $C_{13}$ oxo-process aldehydes to be combined with a bottom fraction arising in the distillation of a crude mixture of $C_4$ to $C_{13}$ oxo-process alcohols before the combined bottom fraction is employed in the process of the invention. In general it is useful to combine those bottom fractions which arise in the distillation of oxo-process aldehydes and oxo-process alcohols having the same carbon number. The advantage of this is that it simplifies the distillative purification of the monohydroxy compounds obtained by means of the process of the invention.

Besides high-boiling byproducts, the bottom fraction may comprise residues of $C_4$ to $C_{13}$ oxo-process aldehydes and/or $C_4$ to $C_{13}$ oxo-process alcohols. Thus, for example, the bottom fraction may comprise residues of $C_4$ to $C_9$ oxo-process aldehydes and/or $C_4$ to $C_9$ oxo-process alcohols. Further, the bottom fraction may comprise, for example, residues of $C_4$ or $C_9$ oxo-process aldehydes and/or $C_4$ or $C_9$ oxo-process alcohols. The bottom fraction may also comprise residues of $C_4$ oxo-process aldehydes and/or $C_4$ oxo-process alcohols.

The distillation of a crude mixture of $C_4$ to $C_{13}$ oxo-process aldehydes or of a crude mixture of $C_4$ to $C_{13}$ oxo-process alcohols takes place continuously or batchwise. The distillation is performed as a standard distillation or as a rectification. The distillation is performed in one or more distillation columns. Generally speaking, it is advantageous to perform the distillation as a rectification, using one or more rectifying columns. If the rectification is performed in two or more rectifying columns, it is advantageous to use a plurality of rectifying columns connected in series—for example, 2, 3 or 4 columns.

As columns for the distillation, or rectification, suitability is possessed for example by tray columns, such as a valve tray column. Columns with packings are generally preferred. Packings comprise, for example, disordered beds or ordered packings. Ordered packings are generally preferred. The number of theoretical plates may be adapted by the skilled person to the desired separation effect, on the basis of his or her art knowledge and by means of a few routine tests.

Advantageous process embodiments for the distillation of a crude mixture of $C_4$ to $C_{13}$ oxo-process aldehydes or of a crude mixture of $C_4$ to $C_{13}$ oxo-process alcohols are disclosed in EP-B1 1 165 480 or in DE-A1 199 14 260, for example. The processes described in EP-B1 1 165 480 and DE-A1 199 14 260 are suitable for the distillation both of a crude mixture of oxo-process aldehydes and of a crude mixture of oxo-process alcohols.

The bottom fraction may be subjected to further distillation, stripping and/or extraction before being used in the process of the invention. The stated process measures may have the effect, for example, of depleting inorganic compounds, residues of the hydroformylation catalyst, and/or other byproducts, and also phosphorus-containing compounds. This may reduce damage to the catalyst in the process of the invention, by coking and/or clogging of the catalyst pores and/or poisoning, for example, thus extending the service life.

If the bottom fraction is subjected to further distillation before being used in the process of the invention, this is done at elevated temperature and reduced pressure. A distillation of this kind takes place, for example, at a temperature of 70 to 220° C. and a pressure of 10 to 500 mbar. The distillate obtained in such a distillation, which includes high-boiling byproducts among other compounds, is then used in the process of the invention.

If a bottom fraction is distilled before it is used in the process of the invention, the distillation may take place in one or more columns. A distillation of this kind may take the form of distillation in a falling-film evaporator or else of a flash distillation. Such a distillation may take place continuously or batchwise.

Hence the bottom fraction, before being used in the process of the invention, may be subjected to continuous or batchwise flash distillation at a temperature of 70 to 220° C. and a pressure of 10 to 500 mbar.

The bottom fraction, before being used in the process of the invention, may also be subjected to continuous or batchwise distillation at a temperature of 70 to 220° C. and a pressure of 10 to 500 mbar in a falling-film evaporator.

In the case of stripping, the bottom fraction is contacted with a stripping medium, in concurrent or countercurrent mode. A stripping medium generally comprises a gas such as air, nitrogen and/or steam. Stripping may be performed by known methods of the prior art.

Extraction is generally performed in the form of a liquid/liquid extraction. Extraction may take place continuously or batchwise. An extraction may comprise one, or two or more, extraction steps, as for example 2, 3 or 4 steps. In each of the extraction steps the extraction medium may be the same or different. In general it is preferred to use water as extraction medium in an extraction step. This water Is preferably demineralized water.

The precise composition of the bottom fraction generally differs greatly according to the location at which the bottom fraction is obtained. Thus the composition of the bottom fraction is dependent, for example, on the starting materials of the hydroformylation or hydrogenation.

If, for example, largely pure n-butyraldehyde is hydrogenated, the bottom fraction which then arises in the distillation of the crude mixture of $C_4$ oxo-process alcohols may include the following compounds among others:

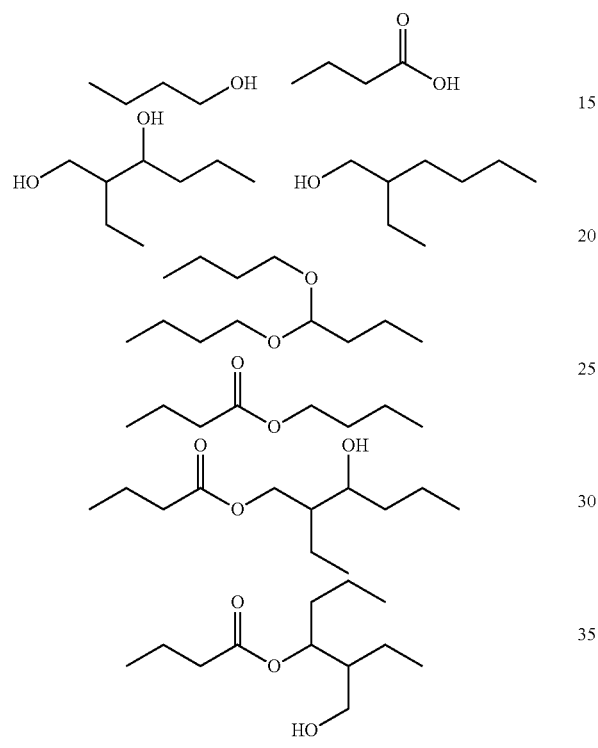

If, for example, a mixture of largely pure n-butyraldehyde and isobutyraldehyde is hydrogenated, the bottom fraction then arising in the distillation of the crude mixture of $C_4$ oxo-process alcohols may include the following compounds among others:

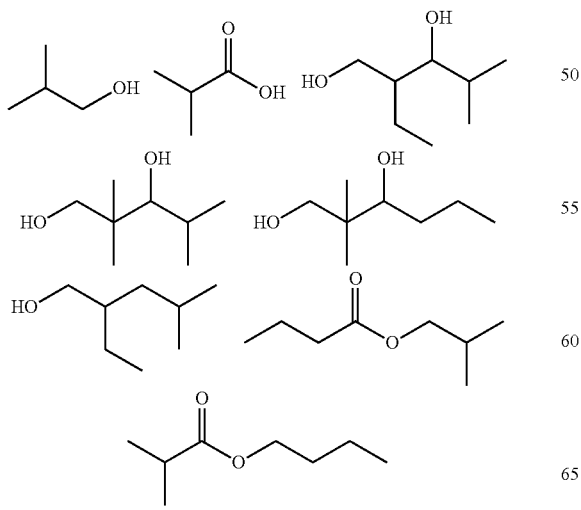

-continued

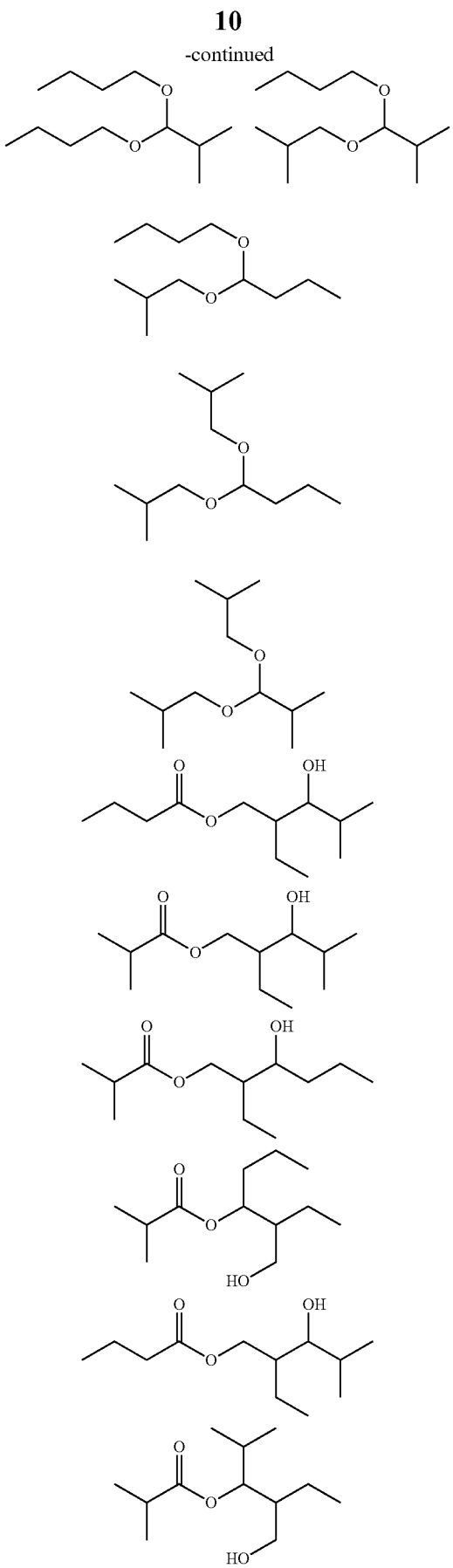

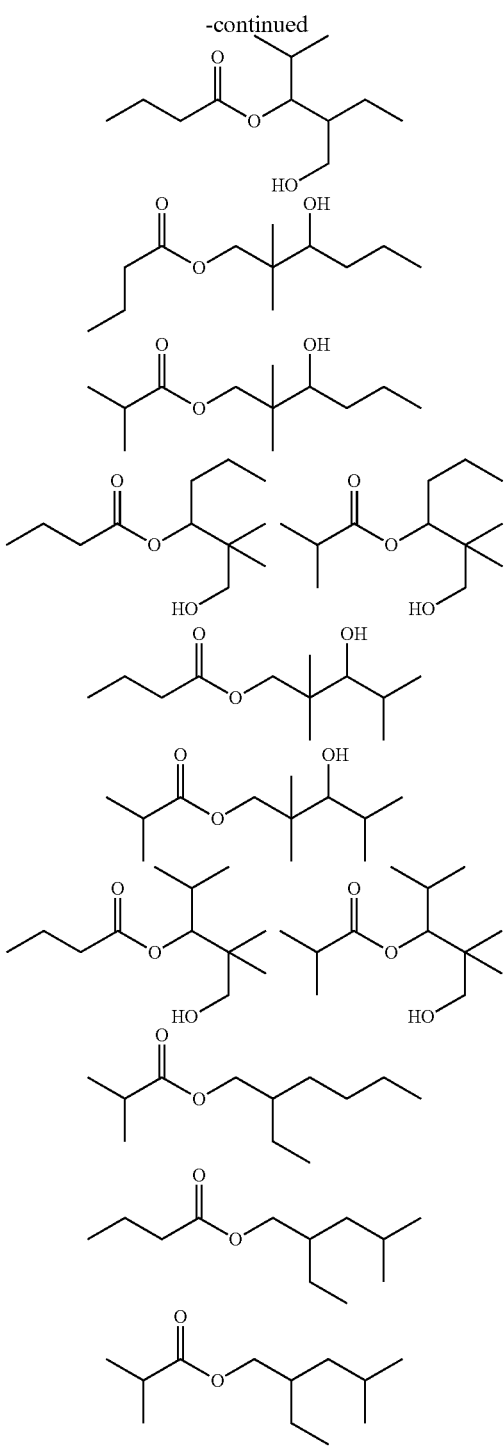

Another subject of the invention, accordingly, is a process for preparing $C_4$ monohydroxy compounds from a bottom fraction arising in the distillation of a crude mixture of $C_4$ oxo-process aldehydes from rhodium-catalyzed hydroformylation, or in the distillation of a crude mixture of $C_4$ oxo-process alcohols, which comprises contacting the bottom fraction in the presence of hydrogen with a catalyst comprising copper oxide (CuO) and aluminum oxide, at a temperature of 150° C. to 300° C. and a pressure of 20 bar to 300 bar and subjecting the resulting crude hydrogenation product to distillation, and the amount of $C_4$ monohydroxy compounds present in the crude hydrogenation product after the hydrogenation being greater than the amount of $C_4$ monohydroxy compounds given stoichiometrically from the hydrogenation of the ester and aldehyde compounds present in the bottom fraction, including the $C_4$ monohydroxy compounds still present in the bottom fraction before the hydrogenation.

According to the process of the invention, the bottom fraction is contacted in the presence of hydrogen with a catalyst. The catalyst is a heterogeneous catalyst. The catalyst comprises copper oxide (CuO) and aluminum oxide. With preference the catalyst as well as copper oxide (CuO) and aluminum oxide comprises one or more oxides of manganese, of lanthanum, of tungsten, of molybdenum, of titanium, of zinc or of zirconium. It is further preferred for the catalyst to comprise, as well as copper oxide (CuO) and aluminum oxide, one or more oxides of manganese, of lanthanum or of zinc. It is particularly preferred for the catalyst to comprise, as well as copper oxide (CuO) and aluminum oxide, one or more oxides of lanthanum or of zinc.

In general the catalyst contains 40 to 95 weight percent of copper oxide (CuO) and 5 to 60 weight percent of aluminum oxide. The catalyst may further comprise up to 30 weight percent of one or more oxides of manganese, lanthanum, tungsten, molybdenum, titanium, zinc or zirconium. Where the catalyst as well as copper oxide and aluminum oxide further comprises one or more oxides of manganese, lanthanum, tungsten, molybdenum, titanium, zinc or zirconium, the sum of the weight fractions adds up to 90 to 100 weight percent. The weight percentages are based on the total weight of the oxidic material present in the catalyst after calcining. The fraction of oxidic material in the catalyst is at least 80 weight percent, based on the total weight of the catalyst after calcining. Hence the fraction of oxidic material in the catalyst, based on the total weight of the catalyst after calcining, is preferably 80 to 100 weight percent, more preferably 90 to 100 weight percent.

It is preferred for the catalyst to comprise 40 to 80 weight percent of copper oxide (CuO), 5 to 60 weight percent of aluminum oxide, and 0 to 30 weight percent of manganese oxide (MnO), lanthanum oxide or zinc oxide. The weight figures are based in each case on the total weight of the oxidic material present in the catalyst after calcining, and add up to a value of 90 to 100 weight percent. The fraction of oxidic material in the catalyst is at least 80 weight percent, based on the total weight of the catalyst after calcining. Hence the fraction of oxidic material in the catalyst, based on the total weight of the catalyst after calcining, is preferably 80 to 100 weight percent, more preferably 90 to 100 weight percent.

A catalyst preferred for the process of the invention and comprising copper oxide (CuO), aluminum oxide, and zinc oxide is disclosed in EP-B1 0901982. The chemical composition of such a catalyst of the kind disclosed in EP-B1 0901982 may vary within wide limits. The atomic Cu:Zn ratio is preferably 1:5 to 5:1, more preferably 1:1 to 4:1, more particularly 2:1 to 3:1. The atomic (Cu+Zn):Al ratio is preferably 99:1 to 70:30, more preferably 95:5 to 80:20. Especially preferred is a Cu:Zn:Al ratio of about 65:25:10. This corresponds to a chemical composition of 67 weight percent CuO, 26.4 weight percent ZnO, and 6.6 weight percent $Al_2O_3$ in the completed catalyst (i.e., based on the total weight of the catalyst after calcining).

Besides the elements copper, zinc, and aluminum, the catalyst may also comprise one or more elements selected from the platinum metals, groups IV, V, and XI, and the lanthanides of the Periodic Table of the Elements. Preferred examples are Pd, Pt, Rh, Ru, Os, Au, Zr, Ti, V, Nb, Ta, and also the lanthanides.

For the preparation of such a Cu—Zn—Al catalyst, for example, first of all a Zn—Al mixed oxide compound is generated and is subsequently converted by calcining into an at least partly acid-insoluble phase, this phase is suspended in acidic solution, and subsequently a Cu—Zn mixed oxide compound is generated in the presence of this phase. Mixed oxide compounds are oxide, hydroxide, carbonate, and hydroxycarbonate compounds. Overall a mixed oxide comprising Zn—Al mixed oxide and Cu—Zn mixed oxide is obtained. This oxide is then dried at temperatures of 20 to 400° C. and calcined at temperatures of 200 to 800° C. Precise embodiments for preparing such a catalyst are disclosed in EP-B1 0901982.

Likewise preferred for the process of the invention is a catalyst which comprises copper oxide (CuO), aluminum oxide, and lanthanum oxide. A catalyst of this kind is disclosed for example in WO 2004/085356. Such a catalyst contains 55 to 75 weight percent copper oxide (CuO), 20 to 30 weight percent aluminum oxide, and 3 to 15 weight percent lanthanum oxide, in the form of oxidic material. The weight figures are based in each case on the total weight of the oxidic material present in the catalyst after calcining, and add up to a value of 90 to 100 weight percent. The fraction of oxidic material in the catalyst is at least 80 weight percent, based on the total weight of the catalyst after calcining. Hence the fraction of oxidic material in the catalyst, based on the total weight of the catalyst after calcining, is preferably 80 to 100 weight percent, more preferably 90 to 100 weight percent.

A catalyst of this kind may after calcining be additionally admixed with metallic copper powder, copper flakes, cement powder, graphite or a mixture thereof, with a fraction of 0.5 to 20 weight percent, based on the total weight of the oxidic material present in the catalyst. If metallic copper powder, copper flakes, cement powder, graphite or a mixture thereof is admixed to the catalyst, the resulting mixture is again calcined at a temperature of 270° C. to 400° C. Cement powder is not considered here to be an oxidic material. Such a catalyst preferably has a chemical composition of 55 to 60 weight percent CuO, 25 to 30 weight percent $Al_2O_3$, 8 to 10 weight percent $La_2O_3$, and 3 to 6 weight percent metallic copper. The weight figures are based in each case on the total weight of the catalyst after calcining and add up to a value of 90 to 100 weight percent.

The production of such catalysts is likewise disclosed in WO 2004/085356. Thus, for example, an aqueous solution of copper nitrate, aluminum nitrate, and lanthanum nitrate is mixed under pH control with an aqueous sodium carbonate solution. The reaction mixture is subsequently washed free of nitrate, dried, and calcined at a temperature of 300° C. The mixture obtained after calcining is then compacted with graphite and the compacted material is mixed with metallic copper and graphite and tabletted. The tablets obtained are finally calcined at 350° C. (2 h).

A catalyst likewise preferred for the process of the invention contains 55 to 70 weight percent copper oxide (CuO), 20 to 35 weight percent aluminum oxide, and 3 to 15 weight percent manganese oxide (MnO). The weight figures are based in each case on the total weight of the oxidic material present in the catalyst after calcining, and add up to a value of 90 to 100 weight percent. The fraction of oxidic material in the catalyst is at least 80 weight percent, based on the total weight of the catalyst after calcining. Hence the fraction of oxidic material in the catalyst, based on the total weight of the catalyst after calcining, is preferably 80 to 100 weight percent, more preferably 90 to 100 weight percent. With particular preference such a catalyst has a chemical composition of 58 to 62 weight percent copper oxide (CuO), 8 to 12 weight percent manganese oxide (MnO), and 28 to 32 weight percent aluminum oxide. The weight figures are based in each case on the total weight of the oxidic material present in the catalyst after calcining, and add up to a value of 90 to 100 weight percent. The fraction of oxidic material in the catalyst is preferably at least 80 weight percent, based on the total weight of the catalyst after calcining. Hence the fraction of oxidic material in the catalyst, based on the total weight of the catalyst after calcining, is preferably 80 to 100 weight percent, more preferably 90 to 100 weight percent.

The production of manganese-containing catalysts is disclosed for example in WO 97/34694. For the production, for example, an aqueous copper nitrate solution ($Cu(NO_3)_2$), an aqueous manganese nitrate solution, and an aqueous sodium aluminate solution ($Na_2Al_2O_4$) are mixed under pH control into an aqueous sodium carbonate solution ($Na_2CO_3$). The precipitate which forms is isolated by filtration, washed, and dried at a temperature of up to 150° C. The dry product is subsequently calcined at a temperature of 300 to 1000° C. Alternatively, for example, an aqueous copper nitrate solution ($Cu(NO_3)_2$) and an aqueous sodium aluminate solution ($Na_2Al_2O_4$) are mixed under pH control into an aqueous sodium carbonate solution ($Na_2CO_3$). The precipitate which forms is isolated by filtration, washed, and dried at a temperature of up to 150° C. The dry product is subsequently calcined at a temperature of 300 to 1000° C. The calcined product is subsequently impregnated with an aqueous manganese solution, an example being manganese chloride solution, and is calcined again at a temperature of 300 to 1000° C. All calcination steps are carried out in the presence of oxygen.

A further catalyst preferred for the process of the invention contains 40 to 60 weight percent copper oxide (CuO) and 60 to 40 weight percent aluminum oxide. The weight figures are based in each case on the total weight of the oxidic material present in the catalyst after calcining, and add up to a value of 90 to 100 weight percent. The fraction of oxidic material in the catalyst is preferably at least 80 weight percent, based on the total weight of the catalyst after calcining. Hence the fraction of oxidic material in the catalyst, based on the total weight of the catalyst after calcining, is preferably 80 to 100 weight percent, more preferably 90 to 100 weight percent.

A catalyst of this kind may be produced for example in analogy to WO 97/34694.

To contact the bottom fraction with a catalyst in the presence of hydrogen, the bottom fraction and hydrogen are introduced into a reactor in which the catalyst is located.

The bottom fraction is introduced in the liquid phase into the reactor. With preference the bottom fraction has been diluted with a liquid inert medium. The advantage of this, for example, is that it allows the viscosity of the bottom fraction to be lowered, so making the fraction easier to convey. The dilution of the bottom fraction with a liquid inert medium may also serve to exert a favorable influence over the removal of heat during the reaction.

Under the reaction conditions, an inert medium does not enter into any reaction with the reactants, products and/or catalyst. A liquid inert medium for example is a long-chain hydrocarbon. The fraction of an inert medium is preferably 10 to 80 weight percent, more preferably 20 to 70 weight percent, and very preferably 25 to 65 weight percent, based on the total weight of bottom fraction and inert medium.

The bottom fraction is preferably contacted with the catalyst in such a way that a total liquid hourly space velocity over the catalyst is from 0.01 to 5 $g_{bottom\ fraction}/(ml_{catalyst}*h)$. It is further preferred that a total liquid hourly space velocity is from 0.3 to 5 $g_{bottom\ fraction}/(ml_{catalyst}*h)$. If the bottom fraction is diluted with a liquid inert medium, it should be ensured that the total liquid hourly space velocity over the catalyst is within the bounds defined above.

Hydrogen is preferably introduced in very high purity into the reactor. Pure hydrogen has a purity of at least 95 weight percent. Impurities in the hydrogen may be methane and/or nitrogen, for example.

Hydrogen is introduced into the reactor at least in the stoichiometric amount relative to the compounds in the bottom fraction that are to be reduced. Hence the amount of hydrogen introduced into the reactor may be 100 to 300 percent of the stoichiometric amount, based on the compounds in the bottom fraction that are to be reduced. With preference the amount of hydrogen is 105 to 200 percent, more preferably 110 to 180 percent, and very preferably 120 to 160 percent. The amount of hydrogen may be, for example, 101, 102, 108, 112, 115, 118, 122, 125, 130, 135, 140, 145, 150 or 155 percent of the stoichiometric amount, based on the compounds in the bottom fraction that are to be reduced.

It is useful to convert the catalyst into an active form before its use in the process of the invention. For this purpose the catalyst, for example, is reduced in the presence of a hydrogen-containing gas according to a temperature program. A hydrogen-containing gas is a gas containing 1 to 99 percent of hydrogen and 99 to 1 percent of a gaseous inert medium such as nitrogen, argon and/or helium. In order, for example, to ensure more effective removal of heat during activation of the catalyst, it is further useful to carry out the activation in the presence of a liquid inert medium. A liquid inert medium is, for example, a long-chain hydrocarbon or a mixture of long-chain hydrocarbons.

Suitable in principle as reactors for the process of the invention are all reactors in which hydrogenation reactions, preferably liquid-phase hydrogenation reactions, can be carried out, and which are suitable for hydrogenation at a temperature of 150 to 300° C. and a pressure of 20 to 300 bar. Hence it is possible, for the process of the invention, to utilize, for example, stirred tank reactors, stirred tank cascades, chamber reactors, bubble columns, loop reactors, trickle film reactors, tray columns, thin-film reactors, jet nozzle reactors, pulsating columns, fixed bed reactors, fixed bed tubular reactors, fixed bed reactors with internal or external heat exchangers, fluidized bed reactors, multistage fluidized bed reactors, moving bed reactors, or any desired combination thereof. Two or more identical or different types of reactor may be connected in series or in parallel. Reactors suitable for the process of the invention are described for example in J. Falbe, Katalysatoren, Tenside und Mineralöladditive, Georg Thieme Verlag, Stuttgart, 1978, pages 30 to 37.

Preferred types of reactor are those in which the catalyst is arranged in a fixed bed or in a heap. It is possible for a reactor to contain a plurality of catalyst fixed beds or heaps in series. In that case the reactor is divided into zones with catalyst (reaction zones) and zones without catalyst, these zones alternating with one another. The number of reaction zones in a reactor may be 2 to 10.

The bottom fraction and hydrogen are introduced into the reactor via one or more feed lines. With preference, bottom fraction and hydrogen are introduced into the reactor via one or more separate feed lines. Although not preferred, it is in general also possible for the bottom fraction and hydrogen to be premixed and introduced into the reactor via one or more common feed lines.

With preference the bottom fraction is introduced into the reactor in trickle mode or in liquid-phase mode. In that case the bottom fraction is introduced into the reactor cocurrently or countercurrently with hydrogen, with preference being given to its cocurrent introduction.

Where a reactor having two or more reaction zones is used for the process of the invention, hydrogen may also be introduced into the reactor between the reaction zones and contacted there with the bottom fraction. An advantage of this, for example, is that the temperature development during the reaction can be controlled more effectively. One advantageous process embodiment is described in EP-A1 0 073 129, for example.

The process of the invention is performed continuously or batchwise, with preference being given to continuous performance.

The process of the invention may be performed adiabatically or nonadiabatically. If the process of the invention is performed adiabatically, it is advantageous to use a reactor having two or more reaction zones. While the reaction in the individual reaction zones proceeds largely adiabatically, colder reactants in the form of hydrogen or fresh bottom fraction can be fed in between the reaction zones. This allows a largely adiabatic reaction regime with enhanced temperature control. One advantageous embodiment of such a process is disclosed in EP-A1 0 073 129, for example.

For the purposes of the present invention, the bottom fraction, hydrogen, and the catalyst are contacted generally at a temperature of 150 to 300° C., preferably 180 to 260° C.

The bottom fraction, hydrogen, and the catalyst are contacted in general at a pressure of 20 to 300 bar, preferably 100 to 300 bar, and more preferably 150 to 280 bar.

With preference the bottom fraction, hydrogen, and catalyst are contacted at a temperature of 150 to 300° C. and a pressure of 100 to 300 bar and more preferably at a temperature of 180 to 260° C. and a pressure of 150 to 280 bar.

The process of the invention gives a reaction mixture which is also referred to as crude hydrogenation product. The crude hydrogenation product from the process of the invention, or from the hydrogenation of the invention, may include, alongside $C_4$ to $C_{13}$ monohydroxy compounds, various byproducts, such as high-boiling byproducts.

The amount of $C_4$ to $C_{13}$ monohydroxy compounds present in the crude hydrogenation product is greater than the stoichiometric amount of $C_4$ to $C_{13}$ monohydroxy compounds resulting from the hydrogenation of the ester and aldehyde compounds present in the bottom fraction, including the $C_4$ to $C_{13}$ monohydroxy compounds already present in the bottom fraction before the hydrogenation.

The calculation of the amount of $C_4$ to $C_{13}$ monohydroxy compounds obtainable according to the process of the invention will be shown by way of example below for n-butanol as the $C_4$ monohydroxy compound. The bottom fraction in this case is obtained in the distillation of a crude mixture of n-butanol.

In a first step, the bottom fraction used in the process of the invention is analyzed to determine whether the components it contains can be traced back formally to $C_4$ or $C_8$ constituents. The analysis is conducted, for example, by GC, the retention times of the individual compounds having been elucidated by GC/MS. The components present in the bottom fraction can then be classed, by way of example, as follows:

n-Butanol: 100% $C_4$
n-Butyl butyrate: 100% $C_4$
n-Butyraldehyde n,n-dibutyl acetal: 100% $C_4$
$C_8$ diols: 100% $C_8$
2-Ethylhexan-1-ol: 100% $C_8$
$C_{12}$ esters: 33% $C_4$ and 67% $C_8$ By summing the components it is possible to determine a $C_4$ fraction, a $C_8$ fraction, and a fraction of unapportioned components in the bottom fraction. The total of n-butanol which is obtained in the crude hydrogenation product is the total $C_4$ yield.

On the assumption that the conversion of the $C_4$ components in the bottom fraction to n-butanol is complete, the figure for the total $C_4$ yield in the crude hydrogenation product can be used to calculate the conversion of the $C_8$ components.

Total $C_4$ yield–$C_4$ fraction in the bottom fraction–fraction of unapportioned components=yield of $C_4$ components through conversion of $C_8$ components.

This calculation enables a statement of the number of $C_8$ components converted to n-butanol. The composition of the crude hydrogenation product may likewise be determined by means of GC/MS, or GC.

The crude hydrogenation product from the process of the invention is subjected to distillation. A distillation is a standard distillation or rectification. The distillation takes place continuously or batchwise. The distillation is performed in one or more distillation columns. In general it is advantageous to perform the distillation as a rectification, using one or more rectifying columns. Where rectification is performed in a plurality of rectifying columns, it is advantageous to use two or more—for example, 2, 3 or 4—rectifying columns in series.

Examples of suitable columns for the distillation, or rectification, are tray columns, such as a valve tray column. Columns with packings are generally preferred. Packings, for example, comprise disordered beds or ordered packings. Ordered packings are generally preferred. The number of theoretical plates may be adapted to the desired separation effect by the skilled person on the basis of his or her art knowledge and through a few routine experiments.

Advantageous embodiments of a process for distilling a crude hydrogenation product from the process of the invention are disclosed in EP-B1 1 165 480 or in DE-A 199 14 260. Although the process disclosed in the EP-B1 is described for the distillation of aldehydes, it may also be utilized for the distillation of monohydroxy compounds.

Where the crude hydrogenation product from the process of the invention still contains high-boiling byproducts, it may be useful to return at least part of this product to the process of the invention before subjecting it to distillation. If the crude hydrogenation product is returned at least in part to the process of the invention, the crude hydrogenation product is divided up, with one part being withdrawn from the process, while the other part is returned to the process of the invention. The ratio between the part withdrawn from the process and the part returned to the process of the invention is preferably 1:1 to 20:1. With preference the ratio is 2:1 to 10:1. The part which is returned to the process of the invention may be mixed with fresh bottom fraction or fed separately to the process of the invention. The ratio between fresh bottom fraction and the part returned to the process of the invention is preferably 1:1 to 1:20. With further preference the ratio is 1:4 to 1:15. With particular preference the ratio is 1:4 to 1:10.

The recycling of at least part of the crude hydrogenation product to the process of the invention allows the process to be operated economically even at relatively low conversions. By means of lower conversions it is possible to reduce the residence time and hence the thermal load on the bottom fraction. This fraction therefore has less of a tendency to form unwanted byproducts which may lead to coking of the catalyst.

If a part is returned to the process of the invention, care should be taken to ensure that the total liquid hourly space velocity over the catalyst is within the bounds defined above.

The part that is withdrawn from the process of the invention is subjected to distillation, preferably to rectification.

Without being tied to this theory, it has been discovered that through the process of the invention it is possible to convert not only ester and aldehyde compounds but also diols and acetals into monohydroxy compounds. The process of the invention, accordingly, can be utilized for obtaining hydrogenation products from a bottom fraction containing high-boiling byproducts, thereby allowing a higher overall yield of hydrogenation products to be achieved. Hydrogenation products are, as defined at the outset, alcohols which originate from the hydrogenation of the hydroformylation products and so have one carbon atom more than the olefins used for the hydroformylation. Since the process of the invention can be carried out in customary reactors suitable for industrial-scale hydrogenations, moreover, it can easily be performed in existing apparatus.

Since, surprisingly, it has been discovered that the process of the invention can also be used to convert diols into monohydroxy compounds, another subject of the present invention is a process for preparing $C_4$ monohydroxy compounds by hydrogenolysis of $C_8$ diols, which comprises contacting $C_8$ diols in the presence of hydrogen with a catalyst comprising copper oxide (CuO) and aluminum oxide, at a temperature of 150 to 300° C. and a pressure of 20 to 300 bar, converting the $C_8$ diols at least partially into $C_4$ monohydroxy compounds, and subjecting the resulting reaction mixture to distillation.

In the process of the invention, $C_8$ diols can be used irrespective of their origin. $C_8$ diols generally comprise an isomer mixture. It is also possible to use $C_8$ diols in the form of individual chemical compounds in the process of the invention.

$C_8$ diols are used preferably as a constituent of mixtures in the process of the invention. Thus, for example, $C_8$ diols may be present in a bottom fraction arising in a distillation of a crude mixture of $C_4$ oxo-process aldehydes from the discharge of rhodium-catalyzed hydroformylation, or in a distillation of a crude mixture of $C_4$ oxo-process alcohols from the discharge from the hydrogenation of a crude mixture of $C_4$ oxo-process aldehydes.

$C_8$ diols are linear or branched. $C_8$ diols preferably have a chemical structure wherein two n-butanols, two isobutanols, or one n-butanol and one isobutanol are formed through hydrogenolysis and associated C—C bond breakage. $C_8$ diols meeting this specification have been set out for example above. An example of a $C_8$ diol which can be converted by hydrogenolysis and associated C—C bond breakage into two n-butanols is 2-ethylhexane-1,3-diol.

The process of the invention for the hydrogenolysis of $C_8$ diols produces n-butanol, isobutanol or a mixture thereof as $C_4$ monohydroxy compounds. The nature of the $C_4$ monohydroxy compounds obtained by the process of the invention is dependent on the structure of the $C_8$ diols used.

According to the process of the invention, $C_8$ diols are contacted in the presence of hydrogen with a catalyst. The catalyst is a heterogeneous catalyst.

The catalyst comprises copper oxide (CuO) and aluminum oxide. With preference the catalyst as well as copper oxide (CuO) and aluminum oxide comprises one or more oxides of manganese, of lanthanum, of tungsten, of molybdenum, of titanium, of zinc or of zirconium. It is further preferred for the catalyst to comprise, as well as copper oxide (CuO) and aluminum oxide, one or more oxides of manganese, of lanthanum or of zinc. It is particularly preferred for the catalyst to comprise, as well as copper oxide (CuO) and aluminum oxide, one or more oxides of lanthanum or of zinc.

In general the catalyst contains 40 to 95 weight percent of copper oxide (CuO) and 5 to 60 weight percent of aluminum oxide. The catalyst may further comprise up to 30 weight percent of one or more oxides of manganese, lanthanum, tungsten, molybdenum, titanium, zinc or zirconium. Where the catalyst as well as copper oxide and aluminum oxide further comprises one or more oxides of manganese, lanthanum, tungsten, molybdenum, titanium, zinc or zirconium, the sum of the weight fractions adds up to 90 to 100 weight percent. The weight percentages are based on the total weight of the oxidic material present in the catalyst after calcining. The fraction of oxidic material in the catalyst is at least 80 weight percent, based on the total weight of the catalyst after calcining. Hence the fraction of oxidic material in the catalyst, based on the total weight of the catalyst after calcining, is preferably 80 to 100 weight percent, more preferably 90 to 100 weight percent.

It is preferred for the catalyst to comprise 40 to 80 weight percent of copper oxide (CuO), 5 to 60 weight percent of aluminum oxide, and 0 to 30 weight percent of manganese oxide (MnO), lanthanum oxide or zinc oxide. The weight figures are based in each case on the total weight of the oxidic material present in the catalyst after calcining, and add up to a value of 90 to 100 weight percent. The fraction of oxidic material in the catalyst is at least 80 weight percent, based on the total weight of the catalyst after calcining. Hence the fraction of oxidic material in the catalyst, based on the total weight of the catalyst after calcining, is preferably 80 to 100 weight percent, more preferably 90 to 100 weight percent.

A catalyst preferred for the process of the invention and comprising copper oxide (CuO), aluminum oxide, and zinc oxide is disclosed in EP-B1 0901982. The chemical composition of such a catalyst of the kind disclosed in EP-B1 0901982 may vary within wide limits. The atomic Cu:Zn ratio is preferably 1:5 to 5:1, more preferably 1:1 to 4:1, more particularly 2:1 to 3:1. The atomic (Cu+Zn):Al ratio is preferably 99:1 to 70:30, more preferably 95:5 to 80:20. Especially preferred is a Cu:Zn:Al ratio of about 65:25:10. This corresponds to a chemical composition of 67 weight percent CuO, 26.4 weight percent ZnO, and 6.6 weight percent $Al_2O_3$ in the completed catalyst (i.e., based on the total weight of the catalyst after calcining).

Besides the elements copper, zinc, and aluminum, the catalyst may also comprise one or more elements selected from the platinum metals, groups IV, V, and XI, and the lanthanides of the Periodic Table of the Elements. Preferred examples are Pd, Pt, Rh, Ru, Os, Au, Zr, Ti, V, Nb, Ta, and also the lanthanides.

For the preparation of such a Cu—Zn—Al catalyst, for example, first of all a Zn—Al mixed oxide compound is generated and is subsequently converted by calcining into an at least partly acid-insoluble phase, this phase is suspended in acidic solution, and subsequently a Cu—Zn mixed oxide compound is generated in the presence of this phase. Mixed oxide compounds are oxide, hydroxide, carbonate, and hydroxycarbonate compounds. Overall a mixed oxide comprising Zn—Al mixed oxide and Cu—Zn mixed oxide is obtained. This oxide is then dried at temperatures of 20 to 400° C. and calcined at temperatures of 200 to 800° C. Precise embodiments for preparing such a catalyst are disclosed in EP-B1 0901982.

Likewise preferred for the process of the invention is a catalyst which comprises copper oxide (CuO), aluminum oxide, and lanthanum oxide. A catalyst of this kind is disclosed for example in WO 2004/085356. Such a catalyst contains 55 to 75 weight percent copper oxide (CuO), 20 to 30 weight percent aluminum oxide, and 3 to 15 weight percent lanthanum oxide, in the form of oxidic material. The weight figures are based in each case on the total weight of the oxidic material present in the catalyst after calcining, and add up to a value of 90 to 100 weight percent. The fraction of oxidic material in the catalyst is at least 80 weight percent, based on the total weight of the catalyst after calcining. Hence the fraction of oxidic material in the catalyst, based on the total weight of the catalyst after calcining, is preferably 80 to 100 weight percent, more preferably 90 to 100 weight percent.

A catalyst of this kind may after calcining be additionally admixed with metallic copper powder, copper flakes, cement powder, graphite or a mixture thereof, with a fraction of 0.5 to 20 weight percent, based on the total weight of the oxidic material present in the catalyst. If metallic copper powder, copper flakes, cement powder, graphite or a mixture thereof is admixed to the catalyst, the resulting mixture is again calcined at a temperature of 270° C. to 400° C. Cement powder is not considered here to be an oxidic material. Such a catalyst preferably has a chemical composition of 55 to 60 weight percent CuO, 25 to 30 weight percent $Al_2O_3$, 8 to 10 weight percent $La_2O_3$, and 3 to 6 weight percent metallic copper. The weight figures are based in each case on the total weight of the catalyst after calcining and add up to a value of 90 to 100 weight percent.

The production of such catalysts is likewise disclosed in WO 2004/085356. Thus, for example, an aqueous solution of copper nitrate, aluminum nitrate, and lanthanum nitrate is mixed under pH control with an aqueous sodium carbonate solution. The reaction mixture is subsequently washed free of nitrate, dried, and calcined at a temperature of 300° C. The mixture obtained after calcining is then compacted with graphite and the compacted material is mixed with metallic copper and graphite and tableted. The tablets obtained are finally calcined at 350° C. (2 h).

A catalyst likewise preferred for the process of the invention contains 55 to 70 weight percent copper oxide (CuO), 20 to 35 weight percent aluminum oxide, and 3 to 15 weight percent manganese oxide (MnO). The weight figures are based in each case on the total weight of the oxidic material present in the catalyst after calcining, and add up to a value of 90 to 100 weight percent. The fraction of oxidic material in the catalyst is at least 80 weight percent, based on the total weight of the catalyst after calcining. Hence the fraction of oxidic material in the catalyst, based on the total weight of the catalyst after calcining, is preferably 80 to 100 weight percent, more preferably 90 to 100 weight percent. With particular preference such a catalyst has a chemical composition of 58 to 62 weight percent copper oxide (CuO), 8 to 12 weight percent manganese oxide (MnO), and 28 to 32 weight percent aluminum oxide. The weight figures are based in each case on the total weight of the oxidic material present in the catalyst after calcining, and add up to a value of 90 to 100 weight percent. The fraction of oxidic material in the catalyst is preferably at least 80 weight percent, based on the total weight of the catalyst after calcining. Hence the fraction of oxidic material in the catalyst, based on the total weight of the catalyst after calcining, is preferably 80 to 100 weight percent, more preferably 90 to 100 weight percent.

The production of manganese-containing catalysts is disclosed for example in WO 97/34694. For the production, for example, an aqueous copper nitrate solution ($Cu(NO_3)_2$), an aqueous manganese nitrate solution, and an aqueous sodium aluminate solution ($Na_2Al_2O_4$) are mixed under pH control into an aqueous sodium carbonate solution ($Na_2CO_3$). The precipitate which forms is isolated by filtration, washed, and dried at a temperature of up to 150° C. The dry product is subsequently calcined at a temperature of 300 to 1000° C. Alternatively, for example, an aqueous copper nitrate solution ($Cu(NO_3)_2$) and an aqueous sodium aluminate solution ($Na_2Al_2O_4$) are mixed under pH control into an aqueous sodium carbonate solution ($Na_2CO_3$). The precipitate which forms is isolated by filtration, washed, and dried at a temperature of up to 150° C. The dry product is subsequently calcined at a temperature of 300 to 1000° C. The calcined product is subsequently impregnated with an aqueous manganese solution, an example being manganese chloride solution, and is calcined again at a temperature of 300 to 1000° C. All calcination steps are carried out in the presence of oxygen.

A further catalyst preferred for the process of the invention contains 40 to 60 weight percent copper oxide (CuO) and 60 to 40 weight percent aluminum oxide. The weight figures are based in each case on the total weight of the oxidic material present in the catalyst after calcining, and add up to a value of 90 to 100 weight percent. The fraction of oxidic material in the catalyst is preferably at least 80 weight percent, based on the total weight of the catalyst after calcining. Hence the fraction of oxidic material in the catalyst, based on the total weight of the catalyst after calcining, is preferably 80 to 100 weight percent, more preferably 90 to 100 weight percent.

A catalyst of this kind may be produced for example in analogy to WO 97/34694.

To contact $C_8$ diols with a catalyst in the presence of hydrogen, $C_8$ diols and hydrogen are introduced into a reactor in which the catalyst is located.

$C_8$ diols are introduced in the liquid phase into the reactor. With preference the $C_8$ diols have been diluted with a liquid inert medium. The advantage of this, for example, is that it allows the viscosity of the $C_8$ diols to be lowered, so making them easier to convey. The dilution of the $C_8$ diols with a liquid inert medium may also serve to exert a favorable influence over the removal of heat during the reaction.

Under the reaction conditions, an inert medium does not enter into any reaction with the reactants, products and/or catalyst. A liquid inert medium for example is a long-chain hydrocarbon. The fraction of an inert medium is preferably 10 to 80 weight percent, more preferably 20 to 70 weight percent, and very preferably 25 to 65 weight percent, based on the total weight of $C_8$ diols and inert medium.

The $C_8$ diols are preferably contacted with the catalyst in such a way that a total liquid hourly space velocity over the catalyst is from 0.01 to 5 $g_{liquid\ phase}/(ml_{catalyst}*h)$. It is further preferred that a total liquid hourly space velocity is from 0.3 to 5 $g_{liquid\ phase}/(ml_{catalyst}*h)$. If the $C_8$ diols are diluted with a liquid inert medium, it should be ensured that the total liquid hourly space velocity over the catalyst is within the bounds defined above.

Hydrogen is preferably introduced in very high purity into the reactor. Pure hydrogen has a purity of at least 95 weight percent. Impurities in the hydrogen may be methane and/or nitrogen, for example.

Hydrogen is introduced into the reactor at least in the stoichiometric amount relative to the $C_8$ diols for hydrogenolytic cleavage. Hence the amount of hydrogen introduced into the reactor may be 100 to 300 percent of the stoichiometric amount, based on the amount of $C_8$ diols for hydrogenolytic cleavage. With preference the amount of hydrogen is 105 to 200 percent, more preferably 110 to 180 percent, and very preferably 120 to 160 percent. The amount of hydrogen may be, for example, 101, 102, 108, 112, 115, 118, 122, 125, 130, 135, 140, 145, 150 or 155 percent of the stoichiometric amount, based on the amount of $C_8$ diols for hydrogenolytic cleavage.

It is useful to convert the catalyst into an active form before its use in the process of the invention. For this purpose the catalyst, for example, is reduced in the presence of a hydrogen-containing gas according to a temperature program. A hydrogen-containing gas is a gas containing 1 to 99 percent of hydrogen and 99 to 1 percent of a gaseous inert medium such as nitrogen, argon and/or helium. In order, for example, to ensure more effective removal of heat during activation of the catalyst, it is further useful to carry out the activation in the presence of a liquid inert medium. A liquid inert medium is, for example, a long-chain hydrocarbon or a mixture of long-chain hydrocarbons.

Suitable in principle as reactors for the process of the invention are all reactors in which hydrogenation reactions, preferably liquid-phase hydrogenation reactions, can be carried out, and which are suitable for hydrogenation at a temperature of 150 to 300° C. and a pressure of 20 to 300 bar. Hence it is possible, for the process of the invention, to utilize, for example, stirred tank reactors, stirred tank cascades, chamber reactors, bubble columns, loop reactors, trickle film reactors, tray columns, thin-film reactors, jet nozzle reactors, pulsating columns, fixed bed reactors, fixed bed tubular reactors, fixed bed reactors with internal or external heat exchangers, fluidized bed reactors, multistage fluidized bed reactors, moving bed reactors, or any desired combination thereof. Two or more identical or different types of reactor may be connected in series or in parallel. Reactors suitable for the process of the invention are described for example in J. Falbe, Katalysatoren, Tenside und Mineralöladditive, Georg Thieme Verlag, Stuttgart, 1978, pages 30 to 37.

Preferred types of reactor are those in which the catalyst is arranged in a fixed bed or in a heap. It is possible for a reactor to contain a plurality of catalyst fixed beds or heaps in series. In that case the reactor is divided into zones with catalyst (reaction zones) and zones without catalyst, these zones alternating with one another. The number of reaction zones in a reactor may be 2 to 10.

The $C_8$ diols and hydrogen are introduced into the reactor via one or more feed lines. With preference, the $C_8$ diols and hydrogen are introduced into the reactor via one or more separate feed lines. Although not preferred, it is in general also possible for the $C_8$ diols and hydrogen to be premixed and introduced into the reactor via one or more common feed lines.

With preference the $C_8$ diols are introduced into the reactor in trickle mode or in liquid-phase mode. In that case the $C_8$ diols are introduced into the reactor cocurrently or countercurrently with hydrogen, with preference being given to their cocurrent introduction.

Where a reactor having two or more reaction zones is used for the process of the invention, hydrogen may also be introduced into the reactor between the reaction zones and contacted there with the $C_8$ diols. An advantage of this, for example, is that the temperature development during the reaction can be controlled more effectively. One advantageous process embodiment is described in EP-A1 0 073 129, for example.

The process of the invention is performed continuously or batchwise, with preference being given to continuous performance.

The process of the invention may be performed adiabatically or nonadiabatically. If the process of the invention is performed adiabatically, it is advantageous to use a reactor having two or more reaction zones. While the reaction in the individual reaction zones proceeds largely adiabatically, colder reactants in the form of hydrogen or fresh $C_8$ diols can be fed in between the reaction zones. This allows a largely adiabatic reaction regime with enhanced temperature control. One advantageous embodiment of such a process is disclosed in EP-A1 0 073 129, for example.

For the purposes of the present invention, the $C_8$ diols, hydrogen, and the catalyst are contacted generally at a temperature of 150 to 300° C., preferably 180 to 260° C.

The $C_8$ diols, hydrogen, and the catalyst are contacted in general at a pressure of 20 to 300 bar, preferably 100 to 300 bar, and more preferably 150 to 280 bar.

With preference the $C_8$ diols, hydrogen, and catalyst are contacted at a temperature of 150 to 300° C. and a pressure of 100 to 300 bar and more preferably at a temperature of 180 to 260° C. and a pressure of 150 to 280 bar.

The process of the invention gives a reaction mixture which is also referred to as crude $C_8$ diol hydrogenation product. The crude $C_8$ diol hydrogenation product from the process of the invention, or from the hydrogenation of the invention, may include, alongside $C_4$ monohydroxy compounds, various byproducts, such as high-boiling byproducts.

The crude $C_8$ diol hydrogenation product is subjected to distillation. A distillation is a standard distillation or rectification. The distillation takes place continuously or batchwise. The distillation is performed in one or more distillation columns. In general it is advantageous to perform the distillation as a rectification, using one or more rectifying columns. Where rectification is performed in a plurality of rectifying columns, it is advantageous to use two or more—for example, 2, 3 or 4—rectifying columns in series.

Examples of suitable columns for the distillation, or rectification, are tray columns, such as a valve tray column. Columns with packings are generally preferred. Packings, for example, comprise disordered beds or ordered packings. Ordered packings are generally preferred. The number of theoretical plates may be adapted to the desired separation effect by the skilled person on the basis of his or her art knowledge and through a few routine experiments.

Advantageous embodiments of a process for distilling a crude $C_8$ diol hydrogenation product are disclosed in EP-B1 1 165 480. Although the process disclosed in the EP-B1 is described for the distillation of aldehydes, it may also be utilized for the distillation of $C_4$ monohydroxy compounds.

Where the crude $C_8$ diol hydrogenation product still contains high-boiling byproducts, it may be useful to return at least part of this product to the process of the invention before subjecting it to distillation. If the crude $C_8$ diol hydrogenation product is returned at least in part to the process of the invention, the crude $C_8$ diol hydrogenation product is divided up, with one part being withdrawn from the process, while the other part is returned to the process of the invention. The ratio between the part withdrawn from the process and the part returned to the process of the invention is preferably 1:1 to 20:1. With preference the ratio is 2:1 to 10:1. The part which is returned to the process of the invention may be mixed with fresh $C_8$ diols or fed separately to the process of the invention. The ratio between fresh $C_8$ diols and the part returned to the process of the invention is preferably 1:1 to 1:20. With further preference the ratio is 1:4 to 1:15. With particular preference the ratio is 1:4 to 1:10.

The recycling of at least part of the crude $C_8$ diol hydrogenation product to the process of the invention allows the process to be operated economically even at relatively low conversions. By means of lower conversions it is possible to reduce the residence time and hence the thermal load on the $C_8$ diols. These diols therefore have less of a tendency to form unwanted byproducts which may lead to coking of the catalyst.

If a part is returned to the process of the invention, care should be taken to ensure that the total liquid hourly space velocity over the catalyst is within the bounds defined above.

The part that is withdrawn from the process of the invention is subjected to distillation.

Another subject of the present invention, accordingly, is a process for preparing n-butanol, isobutanol or a mixture thereof by hydrogenolysis of $C_8$ diols, which comprises contacting $C_8$ diols in the presence of a catalyst at a temperature of 150 to 300° C., preferably 180 to 260° C., and a pressure of 100 to 300 bar, preferably 150 to 280 bar, and reacting the $C_8$ diols at least partially to give n-butanol, isobutanol or a mixture thereof, and subjecting the resulting crude $C_8$ diol hydrogenation product to distillation, where the catalyst comprises 40 to 80 weight percent of copper oxide (CuO), 5 to 60 weight percent of aluminum oxide, and 0 to 30 weight percent of manganese oxide (MnO), lanthanum oxide or zinc oxide, based on the total weight of the oxidic material present in the catalyst after calcining, the sum of the weight fractions adds up to 90 to 100 percent, and the fraction of oxidic material is 80 to 100 weight percent, based on the total weight of the catalyst after calcining.

Likewise a subject of the present invention is the use of the above-disclosed catalysts for the preparation of $C_4$ to $C_{13}$ monohydroxy compounds.

Another subject of the invention, accordingly, is the use of the above-disclosed catalysts in the process of the invention for preparing $C_4$ to $C_{13}$ monohydroxy compounds from a bottom fraction in the presence of hydrogen, where the bottom fraction arises in the distillation of a crude mixture of $C_4$ to $C_{13}$ oxo-process aldehydes from the discharge of cobalt-catalyzed or rhodium-catalyzed hydroformylation, or in the distillation of a crude mixture of $C_4$ to $C_{13}$ oxo-process alcohols, or the use of the above-disclosed catalysts in the process of the invention for preparing n-butanol and/or isobutanol from a bottom fraction in the presence of hydrogen, where the bottom fraction arises in the distillation of a crude mixture of $C_4$ oxo-process aldehydes from rhodium-catalyzed hydroformylation, or in the distillation of a crude mixture of $C_4$ oxo-process alcohols, or the use of the above-disclosed catalysts in the process of the invention for preparing n-butanol and/or isobutanol from a bottom fraction in the presence of hydrogen, where the bottom fraction arises in the distillation of a crude mixture of $C_4$ oxo-process aldehydes from rhodium-catalyzed hydroformylation, or in the distillation of a crude mixture of $C_4$ oxo-process alcohols, and the preparation takes place at a temperature of 180 to 260° C. and a pressure of 150 to 280 bar.

Another subject of the invention is the use of the above-disclosed catalysts in the process of the invention for preparing $C_4$ monohydroxy compounds by hydrogenolysis of $C_8$ diols, or the use of the above-disclosed catalysts in the process of the invention for preparing n-butanol, isobutanol or a mixture thereof by hydrogenolysis of $C_8$ diols, where the $C_8$ diols are present in a bottom fraction which arises in the distillation of a crude mixture of $C_4$ oxo-process aldehydes from the discharge of rhodium-catalyzed hydroformylation, or in the distillation of a crude mixture of $C_4$ oxo-process alcohols, or the use of the above-disclosed catalysts in the process of the invention for preparing n-butanol and/or isobutanol by hydrogenolysis of $C_8$ diols, where the $C_8$ diols are present in a bottom fraction which arises in the distillation of a crude mixture of $C_4$ oxo-process aldehydes from the discharge of rhodium-catalyzed hydroformylation, or in the distillation of a crude mixture of $C_4$ oxo-process alcohols, and the preparation takes place at a temperature of 180 to 260° C. and a pressure of 150 to 280 bar.

Another subject of the invention is the use of a bottom fraction for preparing $C_4$ to $C_{13}$ monohydroxy compounds by the process of the invention. The bottom fraction arises in the distillation of a crude mixture of $C_4$ to $C_{13}$ oxo-process aldehydes from the discharge of cobalt-catalyzed or rhodium-catalyzed hydroformylation or in the distillation of a crude mixture of $C_4$ to $C_{13}$ oxo-process alcohols. With preference it is a crude mixture of $C_4$ to $C_9$ oxo-process aldehydes or $C_4$ to $C_{13}$ oxo-process alcohols. More preferably it is a crude mixture of $C_4$ or $C_9$ oxo-process aldehydes or $C_4$ or $C_9$ oxo-process alcohols. With more particular preference it is a crude mixture of $C_4$ oxo-process aldehydes, such as n-butanal and/or isobutanol, or of $C_4$ oxo-process alcohols, such as n-butanol and/or isobutanol.

Isoheptanol, isooctanol, isononanol, isodecanol, isoundecanol or isotridecanol, and also the corresponding aldehydes deriving from the aforesaid alcohols, are isomer mixtures rather than individual chemical compounds. The composition of the isomer mixtures is generally dependent on the starting compounds used for the preparation and/or on the conditions of preparation. Depending on the starting compounds used for the preparation and/or on the preparation conditions, compositions of isomer mixtures are disclosed by way of example in WO 2015/082676.

EXAMPLES

The examples are intended to serve to illustrate the present invention and not to have any restrictive character thereon.

In all of the examples, hydrogen was used in an excess of 120% to 160%, based on the amount needed stoichiometrically for the hydrogenation and/or hydrogenolysis of the reactants.

The potassium and phosphorus contents were determined by elemental analysis (atomic absorption spectroscopy).

The ester number was determined in analogy to EN ISO 3681.

The acid number was determined in analogy to EN ISO 2114.

The calculation of the yield of $C_4$ to $C_{13}$ monohydroxy compounds obtained from a bottom fraction by means of the process of the invention will be shown by way of example below for n-butanol and isobutanol as the $C_4$ monohydroxy compounds.

In a first step, the bottom fraction passed to the process of the invention is analyzed to determine whether the components it contains can be traced back formally to $C_4$ or $C_8$ constituents. The analysis is conducted by GC, the retention times of the individual compounds having been elucidated by GC/MS.

The components present in the bottom fraction are then classed as follows.

Isobutanol: 100% $C_4$
n-Butanol: 100% $C_4$
n-Butyl butyrate: 100% $C_4$
n-Butyraldehyde n,n-dibutyl acetal: 100% $C_4$
$C_8$ diols: 100% $C_8$
2-Ethylhexan-1-ol: 100% $C_8$
$C_{12}$ esters: 33% $C_4$, 67% $C_8$ Thus, for example, isobutanol, n-butanol, n-butyl butyrate, n-butyraldehyde n,n-dibutyl acetal are traced back formally 100% to $C_4$ constituents. $C_8$ diols and 2-ethylhexan-1-ol, for example, are traced back formally 100% to $C_8$ constituents. $C_{12}$ esters for example are traced back formally 33% to $C_4$ and 67% to $C_8$ constituents.

By summing the components it is possible to determine a $C_4$ fraction, a $C_8$ fraction, and a fraction of unapportioned components in the feed. The total of n-butanol and isobutanol which is obtained in the discharge is the total $C_4$ yield.

On the assumption that the conversion of the $C_4$ components in the feed to n-butanol and isobutanol is complete, the figure for the total $C_4$ yield in the discharge can be used to calculate the conversion of the $C_8$ components as follows:

Total $C_4$ yield–$C_4$ fraction in the feed–fraction of unapportioned components in the feed=yield through conversion of $C_8$ components to $C_4$ components through conversion of $C_8$ components.

By means of this method of calculation it is possible to ascertain how many $C_8$ components are converted into n-butanol and isobutanol. The composition of the discharge is likewise determined by means of GC, the retention times of the individual compounds having been elucidated by GC/MS.

The percentages of the individual components are based on GC area percent.

Example 1

The discharge of rhodium-catalyzed hydroformylation was separated by rectification into n-butyraldehyde and isobutyraldehyde. The n-butyraldehyde thus obtained was passed to a hydrogenation, and the discharge of the hydrogenation was separated by rectification. The bottom fraction arising in this rectification was used as reactant.

Reactant Composition:
3% n-Butanol
3% n-Butyl n-butyrate
9% n-Butyraldehyde n,n-dibutyl acetal
47% $C_8$ diols
12% Ethylhexan-1-ol
21% $C_{12}$ esters
5% Others
500 mg/kg Potassium
100 mg/kg Phosphorus
0.01% Water Ester number of reactant 76 mgKOH/g.

$C_4$ fraction of feed: 22%

$C_8$ fraction of feed: 73%.

The reactant was mixed with hydrogen in excess and the mixture was passed in trickle mode over a reactor filled with a catalyst, comprising 24 wt % aluminum oxide, 72 wt % copper oxide (CuO), and 4 wt % lanthanum oxide, based on the total weight of the catalyst after calcining, at 240° C., at a pressure of 200 bar, and with a catalyst loading of 0.32 $g_{reactant}/(ml_{catalyst} \times h)$.

Discharge Composition:

44% n-Butanol

10% Isobutanol

14% 2-Ethylhexan-1-ol

32% Others 220 mg/kg Potassium 28 mg/kg Phosphorus

Ester number of discharge: 4 mgKOH/g,

Total $C_4$ yield: 54%.

Yield by conversion of $C_8$ components to $C_4$ components: 27%,

Percentage conversion of $C_8$ to $C_4$ components: 37%.

Example 2

The discharge from the rhodium-catalyzed hydroformylation of propene was separated by rectification into n-butyraldehyde and isobutyraldehyde. The n-butyraldehyde thus obtained was passed to a hydrogenation, and the discharge from the hydrogenation was separated by rectification. The bottom fraction arising in this rectification was used as reactant. In comparison to example 1, the reactant was additionally extracted with 3×20 wt % of demineralized water, based on the weight of the reactant. The organic phase was mixed with an excess of hydrogen and the mixture was passed in trickle mode over a reactor filled with a catalyst, comprising 24 wt % aluminum oxide, 72 wt % copper oxide (CuO) and 4 wt % lanthanum oxide, based on the total weight of the catalyst after calcining, at 240° C., at a pressure of 200 bar, and with a catalyst loading of 0.32 $g_{reactant}/(ml_{catalyst} \times h)$.

Discharge Composition:

49% n-Butanol

11% Isobutanol

16% 2-Ethylhexanol

24% Others 130 mg/kg Potassium 28 mg/kg Phosphorus

Ester number of discharge: 7 mgKOH/g.

Total $C_4$ yield: 60%.

Yield by conversion of $C_8$ components to $C_4$ components: 33%.

Percentage conversion of $C_8$ to $C_4$ components: 45%.

By extracting the bottom fraction with water it is possible to reduce the potassium fraction in the discharge and to increase the total yield and therefore the conversion of $C_8$ components to $C_4$ components.

Example 3

The discharge from the rhodium-catalyzed hydroformylation of propene was separated by rectification into n-butyraldehyde and isobutyraldehyde. The n-butyraldehyde thus obtained was passed to a hydrogenation, and the discharge from the hydrogenation was separated by rectification. The bottom fraction arising in this rectification was used as reactant. The reactant was distilled on a falling-film evaporator. The distillate was collected.

Reactant Composition:

4% Butanol

9% n-Butyl n-butyrate

1% n-Butyraldehyde n,n-dibutyl acetal

55% $C_8$ diols

12% 2-Ethylhexan-1-ol

18% $C_{12}$ esters

1% Others 470 mg/kg Potassium 75 mg/kg Phosphorus

Ester number of reactant: 86 mgKOH/g.

Distillate Composition:

4% n-Butanol

8% n-Butyl n-butyrate

1% n-Butyraldehyde n,n-dibutyl acetal

55% $C_8$ diols

12% 2-Ethylhexan-1-ol

18% $C_{12}$ esters

1% Others

<3 mg/kg Potassium 84 mg/kg Phosphorus

Ester number of distillate: 84 mgKOH/g.

Example 4

A reactant distilled as in example 3 was used.

Reactant Composition after Distillation:

2% n-Butanol

7% n-Butyl n-butyrate

2% n-Butyraldehyde n,n-dibutyl acetal

58% $C_8$ diols

13% 2-Ethylhexan-1-ol

18% $C_{12}$ esters

<1% Others

<1 mg/kg Potassium 5 mg/kg Phosphorus

Ester number of reactant: 87 mgKOH/g.

$C_4$ fraction in reactant: 17%.

$C_8$ fraction in reactant: 83%.

The reactant was mixed with hydrogen and a portion of the discharge, and this mixture was passed in trickle mode over a reactor filled with a catalyst, comprising 24 wt % aluminum oxide, 72 wt % copper oxide (CuO), and 4 wt % lanthanum oxide, based on the total weight of the catalyst after calcining, at 240° C., at a pressure of 175 bar, and with a catalyst loading of 0.32 $g_{reactant}/(ml_{catalyst} \times h)$. A portion of the discharge was mixed with the reactant so as to give a total liquid hourly space velocity over the catalyst of 4.7 $g_{liquid}/(ml_{catalyst} \times h)$. A portion of the discharge is accordingly returned to the reactor in a circular regime.

Discharge Composition:

39% n-Butanol

10% Isobutanol

16% 2-Ethylhexan-1-ol

35% Others

<3 mg/kg Potassium 4 mg/kg Phosphorus

Ester number of discharge: 14 mgKOH/g.

Total $C_4$ yield: 49%.

Yield through conversion of $C_8$ components to $C_4$ components: 32%.

Percentage conversion of $C_8$ to $C_4$ components: 39%.

TABLE 1

Overview of the result of examples 1, 2 and 4

| Example | Reactant | | | Products | | |
|---|---|---|---|---|---|---|
| | $C_4$ components | $C_8$ components | Un-components | $C_4$ components | $C_8$ components | Unknown |
| 1 | 22% | 73% | 5% | 54% | 14% | 32% |
| 2 | 22% | 73% | 5% | 60% | 16% | 24% |
| 4 | 17% | 83% | 0% | 49% | 16% | 35% |

Example 5

Reactant Composition:
8% n-Butanol
60% $C_8$ diols
6% 2-Ethylhexan-1-ol
18% $C_{12}$ esters
8% Others
215 mg/kg Potassium
13 mg/kg Phosphorus
Ester number of reactant: 71 mgKOH/g.
Acid number of reactant: 7 mgKOH/g.
$C_4$ fraction of reactant: 14%.
$C_8$ fraction of reactant: 78%.

Catalysts used were as follows:
The figures for weight percent are based on the total weight of the catalyst after calcining.

| Catalyst | Aluminum oxide wt % | Copper oxide (CuO) wt % | Lanthanum oxide wt % | Zinc oxide wt % | Manganese oxide (MnO) wt % | Bulk density |
|---|---|---|---|---|---|---|
| 1 | 30 | 60 | | | 10 | 1.31 g/ml |
| 2 | 24 | 72 | 4 | | | 1.21 g/ml |
| 3 | 51 | 49 | | | | 0.87 g/ml |
| 4 | 5 | 70 | | 25 | | 1.32 g/ml |

Table 2 below reports the compositions of the respective discharge with the corresponding catalyst. As can be seen from the table, the use of catalyst 2 leads to initially high butanol yields (54.2%) and high ester conversion. The other catalysts, especially catalyst 1, do lead to lower butanol yields, but fewer middle-boiling byproducts (sum total of dibutyl ether and others) are formed. The total $C_4$ yield through conversion of $C_8$ components is predominantly greater than 20% and amounts to up to 40%. The relative conversion of $C_8$ to $C_4$ components amounts to up to 74%.

On the basis of the ester number and acid number, maximum butanol yields of 19.7% are possible, on the assumption of the complete hydrogenation of the ester functions of n-butyl and/or isobutyl butyrate and of the complete hydrogenation of butyric acid.

TABLE 2

Composition of the discharge for different catalysts

| Catalyst | Run time h | Temperature °C. | n-Butanol % | Iso-butanol % | 2-Ethyl-hexane-1-ol % | Di-butyl ether % | C8 diols % | C12 esters % | Others % | Butanol yield % | Butanol/by-products | Ester number (standard) mg (KOH)/g | Acid number (standard) mg (KOH)/g | Total C4 yield through conversion of C8 components % | % Conversion of C8 to C4 components % | K content ppm | P content ppm |
|---|---|---|---|---|---|---|---|---|---|---|---|---|---|---|---|---|---|
| 1 | 170.5 | 200 | 41.1 | 15.8 | 6.9 | 2.6 | 18.2 | 3.0 | 12.4 | 49.0 | 7.2 | 13 | 0 | 34.9 | 71.3% | 140 | 7 |
| | 479.2 | 200 | 30.5 | 11.7 | 7.3 | 2.1 | 30.6 | 4.9 | 12.9 | 34.3 | 5.0 | 19 | 0 | 20.2 | 59.0% | 190 | 8 |
| | 569.2 | 210 | 35.9 | 15.1 | 8.0 | 3.3 | 17.4 | 3.7 | 16.6 | 43.0 | 3.7 | 20 | 0 | 29.0 | 67.3% | n.d. | n.d. |
| | 975.45 | 200 | 18.9 | 7.3 | 7.1 | 1.3 | 42.8 | 9.6 | 12.8 | 18.3 | 3.1 | 41 | 0 | 4.2 | 23.1% | n.d. | n.d. |
| 2 | 160.5 | 200 | 43.3 | 18.9 | 7.4 | 3.3 | 9.6 | 0.5 | 17.0 | 54.2 | 4.5 | 0 | 0 | 40.2 | 74.1% | 85 | 7 |
| | 497.5 | 200 | 34.4 | 15.1 | 8.5 | 3.4 | 18.3 | 0.7 | 19.5 | 41.6 | 2.8 | 4 | 0 | 27.5 | 66.2% | 175 | 8 |
| | 574 | 210 | 38.2 | 17.8 | 8.7 | 4.0 | 9.2 | 0.5 | 21.6 | 48.1 | 2.8 | 2 | 0 | 34.0 | 70.8% | n.d. | n.d. |
| | 976 | 200 | 30.4 | 14.0 | 8.0 | 3.4 | 24.3 | 1.5 | 18.4 | 36.5 | 2.7 | 10 | 0 | 22.5 | 61.5% | n.d. | n.d. |
| 3 | 160.5 | 200 | 31.5 | 13.5 | 9.4 | 2.2 | 18.7 | 1.7 | 23.0 | 37.1 | 2.2 | 6 | 0 | 23.0 | 62.1% | 18 | 5 |
| | 497.5 | 200 | 30.5 | 13.2 | 9.0 | 3.1 | 21.7 | 2.0 | 20.5 | 35.8 | 2.3 | 8 | 0 | 21.8 | 60.8% | 160 | 6 |
| | 574 | 210 | 34.4 | 16.1 | 9.4 | 3.9 | 11.4 | 1.2 | 23.5 | 42.6 | 2.2 | 7 | 0 | 28.6 | 67.0% | n.d. | n.d. |
| | 970.5 | 200 | 27.8 | 13.1 | 8.4 | 3.3 | 25.6 | 2.5 | 19.3 | 32.9 | 2.3 | 13 | 0 | 18.9 | 57.4% | n.d. | n.d. |
| 4 | 160.5 | 200 | 30.6 | 13.7 | 10.3 | 3.7 | 14.2 | 0.5 | 26.9 | 36.4 | 1.6 | 0 | 0 | 22.3 | 61.4% | 150 | 7 |
| | 497.5 | 200 | 29.1 | 12.6 | 10.0 | 3.8 | 18.8 | 0.8 | 24.8 | 33.8 | 1.7 | 5 | 0 | 19.7 | 58.4% | 195 | 7 |
| | 574 | 210 | 31.5 | 14.9 | 10.2 | 4.4 | 10.8 | 0.7 | 27.6 | 38.4 | 1.6 | 3 | 0 | 24.4 | 63.4% | n.d. | n.d. |
| | 976 | 200 | 25.6 | 11.9 | 9.2 | 3.9 | 24.3 | 1.6 | 23.6 | 29.5 | 1.5 | 10 | 0 | 15.5 | 52.4% | n.d. | n.d. |
| Feed | — | — | 7.9 | 0.0 | 5.5 | 0.0 | 59.9 | 18.4 | 8.2 | — | — | 71 | 7 | — | — | 215 | 13 |

The reactant was mixed with hydrogen and the mixture was passed in liquid-phase mode over a reactor filled with a catalyst, at 220° C., at a pressure of 175 bar, and with a catalyst loading of 3.3 $g_{liquid}/(ml_{catalyst} \times h)$. The reactant stream was mixed with a partial stream composed of the discharge in a ratio of 1:10, and this mixture was supplied to the reactor. Hydrogen was supplied to the combined stream in excess.

The feed already contains around 8% of butanols. These are subtracted from the total of the n-butanols and isobutanols to determine the amount of n-butanols and isobutanols newly formed during the reaction.

Example 8

2 g of a catalyst containing 24 wt % aluminum oxide, 72 wt % copper oxide, and 4 wt % lanthanum oxide, based on the total weight of the catalyst after calcining, were charged to an autoclave and activated under hydrogen pressure. Then 100 g of 2-ethylhexane-1,3-diol were added, and the contents were maintained under a hydrogen pressure of 175 bar at 220° C. for 8 hours. Samples were taken from the liquid phase of the reactor and were analyzed by gas chromatography. The results obtained were as follows:

| Time in hours | Yield of 2-ethylhexane-1,3-diol in % | Yield of n-butanol in % |
|---|---|---|
| 0 | 100 | 0 |
| 2 | 62 | 17 |
| 5 | 27 | 32 |
| 8 | 12 | 38 |

Example 9

The discharge from the cobalt-catalyzed hydroformylation of isooctene was separated from the hydroformylation catalyst and then passed to a hydrogenation, and the discharge from the hydrogenation was separated by rectification. The bottom fraction arising in this rectification was used as reactant. The reactant was analyzed as follows:
1% Isononanol
99% High boilers
Ester number of reactant: 55 mgKOH/g.
Acid number of reactant: 12 mgKOH/g.
The reactant was mixed with hydrogen in excess and this mixture was passed in trickle mode over a reactor filled with a catalyst containing 24 wt % aluminum oxide, 72 wt % copper oxide (CuO), and 4 wt % lanthanum oxide, based on the total weight of the catalyst after calcining, at 200° C., at a pressure of 200 bar, and with a catalyst loading of 0.3 $g_{reactant}/(ml_{catalyst} \times h)$.
The discharge was analyzed as follows:
32% Isononanol
Ester number of discharge: 17 mgKOH/g.
Acid number less than 1 mgKOH/g.
The hydrogenation of the acid formed about 3.5% of isononanol, and the hydrogenation of the ester 19% of isononanol. In total, however, 31% of isononanol was formed, thus indicating the conversion of other high boilers.

The invention claimed is:

1. A process for preparing $C_4$ to $C_{13}$ monohydroxy compounds from a bottom fraction arising in the distillation of a crude mixture of $C_4$ to $C_{13}$ oxo-process aldehydes from cobalt-catalyzed or rhodium-catalyzed hydroformylation, or in the distillation of a crude mixture of $C_4$ to $C_{13}$ oxo-process alcohols, which comprises contacting the bottom fraction in the presence of hydrogen with a catalyst comprising copper oxide (CuO) and aluminum oxide, at a temperature of 180° C. to 260° C. and a pressure of 150 bar to 280 bar and subjecting the resulting crude hydrogenation product to distillation, and the amount of $C_4$ to $C_{13}$ monohydroxy compounds present in the crude hydrogenation product after the hydrogenation being greater than the amount of $C_4$ to $C_{13}$ monohydroxy compounds given stoichiometrically from the hydrogenation of the ester and aldehyde compounds present in the bottom fraction, including the $C_4$ to $C_{13}$ monohydroxy compounds still present in the bottom fraction before the hydrogenation.

2. The process according to claim 1, wherein the catalyst comprises copper oxide (CuO) with a fraction of 40 to 80 weight percent, aluminum oxide with a fraction of 5 to 60 weight percent, and 0 to 30 weight percent of manganese oxide (MnO), lanthanum oxide or zinc oxide, the weight percentages are based on the total weight of the oxidic material present in the catalyst after calcining, the sum of the weight fractions adds up to 90 to 100 percent, and the fraction of oxidic material in the catalyst is at least 80 weight percent, based on the total weight of the catalyst after calcining.

3. The process according to claim 1, for producing $C_4$ to $C_9$ monohydroxy compounds from a bottom fraction arising in the distillation of a crude mixture of $C_4$ to $C_9$ oxo-process aldehydes from cobalt-catalyzed or rhodium-catalyzed hydroformylation, or in the distillation of a crude mixture of $C_4$ to $C_9$ oxo-process alcohols.

4. The process according to claim 3, for producing n-butanol and/or isobutanol from a bottom fraction arising in the distillation of a crude mixture of $C_4$ oxo-process aldehydes from rhodium-catalyzed hydroformylation, or in the distillation of a crude mixture of $C_4$ oxo-process alcohols.

5. The process according to claim 1, wherein the bottom fraction, before being contacted with hydrogen and a catalyst, is subjected to extraction, distillation or stripping.

6. The process according to claim 1, wherein the bottom fraction, before being contacted with hydrogen and a catalyst, is subjected to extraction and distillation.

7. The process according to claim 1, wherein a part of the crude hydrogenation product obtained from the hydrogenation is returned to the disclosed process and a part of the crude hydrogenation product obtained from the hydrogenation is subjected to distillation.

8. A process for preparing $C_4$ monohydroxy compounds by hydrogenolysis of $C_8$ diols, which comprises contacting $C_8$ diols in the presence of hydrogen with a catalyst comprising copper oxide and aluminum oxide, at a temperature of 150° C. to 300° C. and a pressure of 20 bar to 300 bar, reacting the $C_8$ diols at least partially to give $C_4$ monohydroxy compounds, and subjecting the resulting crude $C_8$ diol hydrogenation product to distillation.

9. A process for preparing $C_4$ monohydroxy compounds from the bottom fraction arising in the distillation of a crude mixture of $C_4$ oxo-process aldehydes from rhodium-catalyzed hydroformylation or in the distillation of a crude mixture of $C_4$ oxo-process alcohols, which comprises contacting the bottom fraction in the presence of hydrogen with a catalyst comprising copper oxide and aluminum oxide, at a temperature of 150° C. to 300° C. and a pressure of 20 bar to 300 bar and subjecting the resulting crude hydrogenation product to distillation, and the amount of n-butanol, isobutanol or a mixture thereof present in the crude hydrogenation product after the hydrogenation being greater than the amount of n-butanol, isobutanol or a mixture thereof given stoichiometrically from the hydrogenation of the ester and aldehyde compounds present in the bottom fraction, including the $C_4$ monohydroxy compounds still present in the bottom fraction before the hydrogenation.

* * * * *